(12) United States Patent
Schowalter et al.

(10) Patent No.: US 11,440,818 B2
(45) Date of Patent: *Sep. 13, 2022

(54) FLUID TREATMENT REACTOR

(71) Applicant: CRYSTAL IS, INC., Green Island, NY (US)

(72) Inventors: Leo Schowalter, Latham, NY (US); Rajul Randive, Niskayuna, NY (US); Steven Berger, Newburyport, MA (US)

(73) Assignee: Crystal IS, Inc., Green Island, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/115,737

(22) Filed: Dec. 8, 2020

(65) Prior Publication Data

US 2021/0087078 A1 Mar. 25, 2021

Related U.S. Application Data

(63) Continuation-in-part of application No. 16/855,939, filed on Apr. 22, 2020.

(60) Provisional application No. 62/836,793, filed on Apr. 22, 2019.

(51) Int. Cl.
*C02F 1/32* (2006.01)
*A61L 2/26* (2006.01)
*A61L 2/10* (2006.01)

(52) U.S. Cl.
CPC ............... *C02F 1/325* (2013.01); *A61L 2/10* (2013.01); *A61L 2/26* (2013.01); *A61L 2202/11* (2013.01); *A61L 2202/122* (2013.01); *A61L 2202/123* (2013.01); *C02F 2201/3222* (2013.01); *C02F 2201/3227* (2013.01); *C02F 2201/3228* (2013.01); *C02F 2303/04* (2013.01); *C02F 2307/06* (2013.01)

(58) Field of Classification Search
CPC .............. C02F 1/325; C02F 2303/04; C02F 2201/3222; C02F 2201/3228; A61L 2/10; A61L 2/26; A61L 2202/11; A61L 2202/122; B01J 19/123
See application file for complete search history.

(56) References Cited

U.S. PATENT DOCUMENTS

2020/0392019 A1* 12/2020 Benzerrouk ............ C02F 1/325

* cited by examiner

*Primary Examiner* — Lessanework Seifu
(74) *Attorney, Agent, or Firm* — Nutter McClennen & Fish LLP

(57) ABSTRACT

A system for disinfecting fluid includes a plurality of fluid reactors. Each of the fluid reactors includes at least one UVC LED. The UVC LED includes an LED chip configured to emit UVC radiation and a package coupled with the LED chip. The LED chip has a top surface that defines a chip top surface area. The top surface is formed from a semiconductor material having an index of refraction. The fluid reactor has at least one wall that defines a chamber configured to contain the fluid. The at least one wall has an aperture configured to receive UVC radiation into the chamber. The aperture extends through the at least one wall. The aperture has an aperture area that is (1) smaller than a top surface area of the package and (2) equal to or larger than the chip top surface area.

20 Claims, 23 Drawing Sheets
(20 of 23 Drawing Sheet(s) Filed in Color)

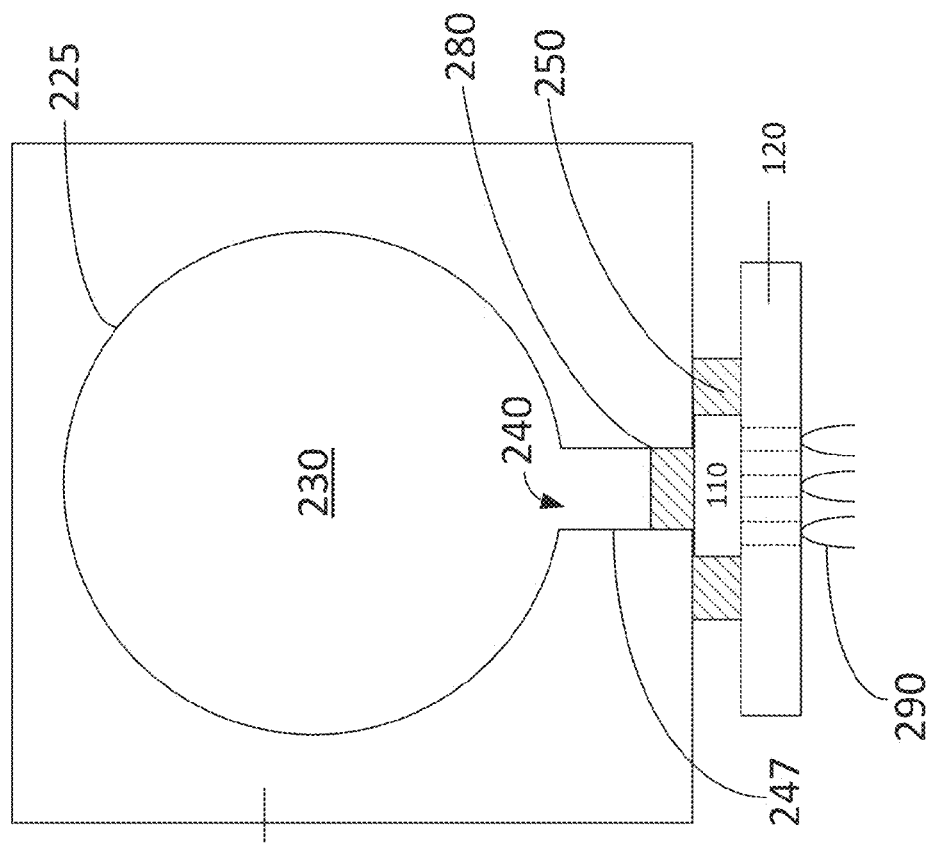
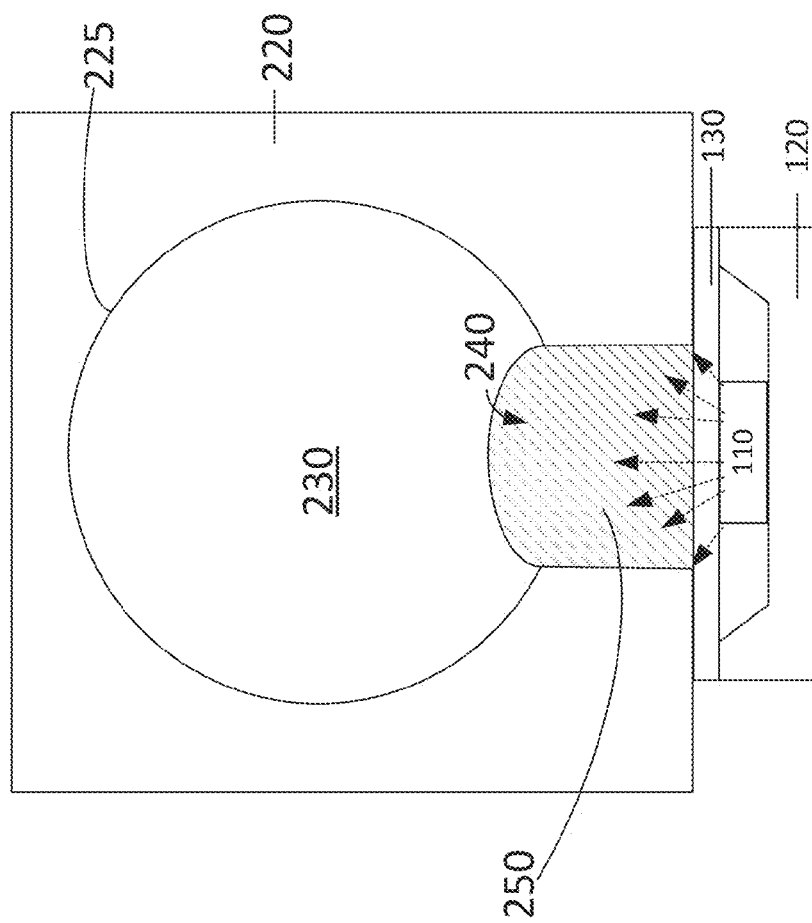
*FIG. 6F*
*FIG. 6E*

FLUID TREATMENT REACTOR

PRIORITY

This patent application is a continuation-in-part of U.S. patent application Ser. No. 16/855,939 filed Apr. 22, 2020, which claims priority from provisional U.S. patent application No. 62/836,793, filed Apr. 22, 2019, both entitled "FLUID TREATMENT REACTOR," and naming Leo J. Schowalter, Rajul Randive, and Steven Berger as inventors, the disclosures of which are both incorporated herein, in their entireties, by reference.

FIELD OF THE INVENTION

Various embodiments of the invention generally relate to fluid treatment and, more particularly, various embodiments relate to using ultraviolet light for water treatment.

BACKGROUND OF THE INVENTION

Fluids, including liquid water, are commonly used for many domestic and industrial purposes, such as drinking, food preparation, manufacturing, processing of chemicals, and cleansing. It is often necessary to purify a liquid prior to its use. Filters such as ceramic filters are typically used to remove particulate and chemical impurities from liquids. In addition, a liquid can be exposed to UV radiation to neutralize microorganisms and deleterious pathogens that may be present in the liquid, e.g., bacteria, viruses, and protozoa. Exposure to certain wavelengths of light can disrupt the DNA of many cellular microorganisms—virtually destroying them or rendering them substantially harmless. The exposure to UV radiation can also substantially prohibit the growth and/or reproduction of microorganisms in the liquid.

A system that uses UV radiation to irradiate fluids is often known in the art as a "UV reactor." Undesirably, conventional UV reactors typically suffer from various disadvantages. Specifically, UV light is difficult to extract efficiently from UV light sources, such as light-emitting diodes (LEDs). Additionally, conventional UV reactors often only successfully utilize a fraction of the UV output of such light sources for disinfection (i.e., only a small fraction of emitted UV light is successfully introduced into the liquid to be treated). In addition, UV LEDs often generate a significant amount of heat, particularly since they must frequently be operated at higher currents (generating larger output fluxes) to compensate for inefficient light extraction.

SUMMARY OF VARIOUS EMBODIMENTS

In accordance with one embodiment of the invention, a system for disinfecting fluid includes a plurality of fluid reactors. Each of the fluid reactors includes at least one UVC LED. The UVC LED includes an LED chip configured to emit UVC radiation and a package coupled with the LED chip. The LED chip has a top surface that defines a chip top surface area. The top surface is formed from a semiconductor material having an index of refraction. The fluid reactor has at least one wall that defines a chamber configured to contain the fluid. The at least one wall has an aperture configured to receive UVC radiation into the chamber. The aperture extends through the at least one wall. The aperture has an aperture area that is (1) smaller than a top surface area of the package and (2) equal to or larger than the chip top surface area.

In various embodiments, the plurality of reactors are arranged in-series. In some embodiments, the plurality of reactors are arranged in-parallel. Furthermore, in some embodiments, the plurality of reactors are arranged in a combination thereof (i.e., in-series and in-parallel).

The UVC LED may be of the type having an exposed top surface. Alternatively, the UVC LED may be on the type having a lidded top surface. The system may be configured to couple more than 60% of the total output radiation of the LED into the fluid reactor. To that end the top surface of the LED chip may be less than 5 millimeters away from an opening of the aperture.

The system may also include an optical coupler configured to contact at least a portion of the LED. The optical coupler may be configured to form a fluid seal with the aperture. Preferably, the optical coupler is UV transparent, UV resistant, and has an index of refraction that is greater than an index of refraction of water.

The LED has an estimated total output radiation at a given UVC wavelength when used in ambient air. The system is configured to increase the total output radiation at the given UVC wavelength over the estimated output power. To that end, the LED chip is intimately coupled with the optical coupler. Thus, the optical coupler is configured to increase the total output radiation of the LED as compared to ambient air. Additionally, the optical coupler may have a distal portion, which is substantially convex. In some embodiments the distal portion may extend into the chamber. The optical coupler may form a fluid tight seal with the chamber and/or the aperture.

Among other advantages, the optical coupler is configured to increase the total output radiation of the LED as compared to ambient air. To that end, in some embodiments, the index of refraction of the optical coupler is approximately the same as the index of refraction of the semiconductor material. Alternatively, the index of refraction of the optical coupler may be less than the index of refraction of the semiconductor material. Preferably, the optical coupler is formed of a thermally conductive material, such as PTFE and/or silicone The optical coupler has a proximal portion that may be coupled with the LED chip, and a distal portion that may extend into the chamber. The distal portion may have a convex shape configured to reduce the amount of photons reflected from an optical coupler-fluid interface.

The surface defining the aperture may be formed of a UV reflective material and/or may have a UV reflective coating. The UV reflective material may be an aluminum coating. Additionally, illustrative embodiments may include a plurality of apertures extending through the at least one wall. The aperture may contact the optical coupler.

In some embodiments, the aperture area is smaller than a top surface area of the package. The package may approximately 5 mm long and/or 5 mm wide. However, in some other embodiments, the aperture may have an area smaller than the chip top surface area. In illustrative embodiments, the chip top surface area is defined by a perimeter having a width of less than about 1 mm, and a length of less than about 1 mm. The aperture may have a width of less than about 1 mm, and/or a length of less than about 1 mm. The aperture may have a diameter of about 0.06 cm to about 0.8 cm. More preferably, the aperture has a diameter of about 0.08 cm to about 0.5 cm. The inner surface area of the wall and the aperture area add to produce a total area. The aperture area may be between about 0.0001% and about 17% of the total area. The aperture area may be greater than about 0.025% of the total area. Additionally, or alternatively, the aperture area may be less than about 0.77% of the total area.

In accordance with another embodiment, a system for disinfecting fluid using UVC LEDs includes a plurality of UVC LEDs. Each of the UVC LEDs includes an LED chip configured to emit UVC radiation and a package coupled with the LED chip. Each of the LED chips has a respective radiation emission surface. The system further includes a plurality of fluid reactors. Each of the fluid reactors includes at least one wall defining a chamber configured to house the fluid. The at least one wall defines a wall area. The chamber has a fluid volume of between about 0.004 $cm^3$ and 20 $cm^3$. For example, the chamber may be shaped like a sphere having a diameter of between about 0.2 cm and about 3.4 cm. The at least one wall has an aperture through which the emitted UVC radiation enters the chamber. The aperture has an aperture area. The wall area and the aperture area add to produce a total area. The aperture area is between 0.0001% and 17 percent of the total area.

The optical coupler is configured to optically couple the UVC LED and the fluid reactor. The optical coupler is UV transparent. For example, the optical coupler may be at least 75% UV transparent. The optical coupler has an index of refraction that is greater than the index of refraction of the fluid. The optical coupler may be positioned between the chamber and the LED chip.

In some embodiments, the LED includes a quartz window on the package. The optical coupler may contact the quartz window. For example, the optical coupler may contact the top of the quartz window. Additionally, or alternatively, the optical coupler may be between the quartz window and the chip. The LED may include an exposed semiconductor surface. The optical coupler may contact the exposed semiconductor surface.

Among other things, the optical coupler may be used to seal the chamber. Additionally, or alternatively, the optical coupler may be used to conduct heat into the aperture and/or the chamber. Accordingly, the system is configured to operate without a heat-sink.

In some embodiments, the aperture area may be greater than about 0.025% of the total area. Additionally, or alternatively, the aperture area may be less than about 0.77% of the total area.

In accordance with yet another embodiment, a method treats fluid. The method provides a plurality of fluid reactors positioned in-series and/or in-parallel. Each of the reactors has at least one wall defining a chamber configured to house fluid therein. The at least one wall defines a wall area. The chamber has a fluid volume of between about 1 $cm^3$ and 10 $cm^3$. The at least one wall has an aperture through which the emitted UVC radiation enters the chamber. The aperture has an aperture area. The wall area and aperture area add to produce a total area. The aperture area is between about 1 percent and about 25 percent of the total area. The method also provides a respective UVC LED configured to emit UVC radiation into a respective fluid reactor. The UVC LED includes an LED chip configured to emit UVC radiation and a package coupled with the LED chip. The LED chip has a radiation emission surface. The method positions the optical coupler in the aperture between the UVC LED and the chamber in each reactor. The method then disinfects the fluid in each reactor by activating the respective UVC LED.

Among other ways, all of the UVC LEDs may be dosed simultaneously. Additionally, the activating may be periodic. Among other things, the method may produce a reduction equivalent dose that is greater than 20 $mJ/cm^2$ dose when the chamber has less than about 10 cc volume and fluid flow rate that is greater than about 0.5 L/min. Furthermore, the chamber may be in the shape of a sphere having a radius of about 0.1 cm to about 10 cm.

The method may further conduct heat from the radiation emission surface of the LED chip and/or the top surface of the LED package. To that end, thermally conductive material may be positioned on the radiation emission surface of the chip and/or the top surface of the package. Additionally, or alternatively, the optical coupler may be formed from sapphire.

The LED package may be unlidded. The method may seal the chamber and/or aperture using the package (e.g., the top surface of the package). To that end, the method may position the package into a package fit portion of the wall of the chamber.

BRIEF DESCRIPTION OF THE DRAWINGS

The patent or application file contains at least one drawing executed in color. Copies of this patent with color drawing(s) will be provided by the Patent and Trademark Office upon request and payment of necessary fee.

Those skilled in the art should more fully appreciate advantages of various embodiments of the invention from the following "Description of Illustrative Embodiments," discussed with reference to the drawings summarized immediately below.

FIG. 6E schematically shows a cross-section of the UV reactor having an aperture area that is larger than the radiation emission surface area, in accordance with illustrative embodiments of the invention.

FIG. 6F schematically shows a cross-section of the UV reactor having an aperture area that is smaller than the radiation emission surface area, in accordance with illustrative embodiments of the invention.

DESCRIPTION OF ILLUSTRATIVE EMBODIMENTS

Figure 1A:
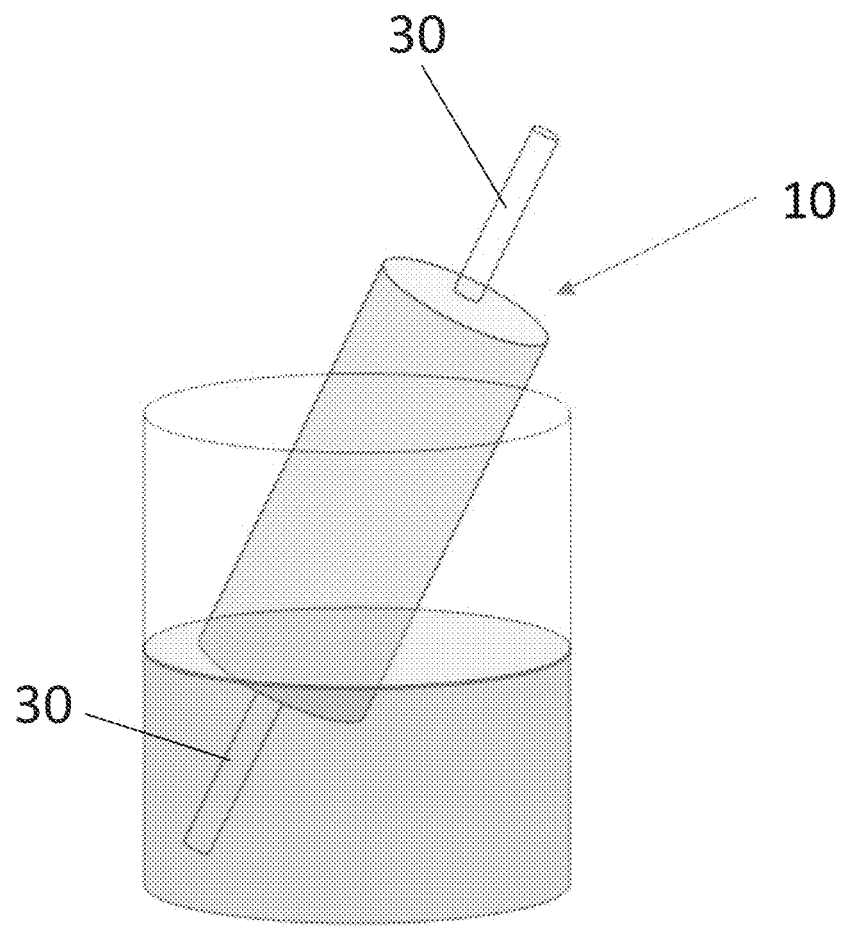
FIG. 1A schematically shows a UV reactor implemented as part of a straw in accordance with illustrative embodiments of the invention.

In illustrative embodiments, a UV reactor efficiently disinfects fluid in its chamber, making it particularly suitable to applications for small reactors. The small UV reactor can be used, for example, in portable devices, such as in a cup or integrated with a straw. Small UV reactors have a short path length for the radiation (i.e., before the radiation contacts a wall of the reactor). Various embodiments thus increase the average reflectivity of the chamber for small volume reactors. Additionally, illustrative embodiments reduce the amount of UV light that escapes the reflective reactor chamber (e.g., an aperture in the chamber wall which allows light to escape has the same effect as if the light were absorbed by that portion of the chamber), effectively increasing the percentage of UV light absorbed by the fluid and/or pathogens in the fluid. To that end, the inventors discovered, contrary to conventional wisdom, that significantly reducing the size of a light aperture for a small reactor increases the reduction equivalent dose (effectiveness of the reactor). Furthermore, the inventors discovered that an optical coupler can be used to further increase the efficiency of the reactor.

Additionally, as described further below, some embodiments use an optical coupler to augment light extraction from a UV LED. When compared to air, the optical coupler, which preferably has a higher index of refraction than that of air and/or the fluid being treated, increases the amount of UV light that escapes the chip. This can be accomplished by reducing index of refraction mismatches at the radiation emission surface interface. Furthermore, the optical coupler is formed of a material that is configured to be in intimate contact with the UV LED chip. Illustrative embodiments intimately couple the coupling material with the semiconductor surface by bringing the coupling material within a fraction of a wavelength to the semiconductor surface. It should be understood that intimate coupling is dependent on the wavelength of the light that is to be emitted. Intimate coupling is difficult to achieve for UV wavelengths across the entire area of the LED chip surface simply by pressing the LED up against a quartz window. The difficulty arises because small variations (e.g., on the order of 0.1 microns across a 1 mm square surface) in the flatness of either the semiconductor surface or the quartz window introduce an additional interface (e.g., with an index of refraction of 1), which causes total internal reflection at that surface. Total internal reflection at the surface significantly reduces the amount of light transmitted into the optical coupler.

As a further advantage, the optical coupler is configured to form a fluid seal with an aperture of the chamber and to conduct heat from the top radiation-emitting surface of the LED into the aperture and/or chamber. Accordingly, the same fluid that the LED is configured to disinfect may be used to cool the LED. By cooling the LED from the top radiation-emitting surface, illustrative embodiments may avoid the use of a traditional bottom-mounted heat sink, and therefore, maintain a smaller form factor, lower assembly costs, and smaller bill of materials. Details of illustrative embodiments are discussed below.

FIG. 1A schematically shows one use of a smaller UV reactor 10 configured in accordance with illustrative embodiments of the invention. Preferably, the reactor 10 has a small footprint, is light weight, and/or has on-demand use capacity. In addition, the UV reactor 10 preferably adds no noticeable smell or taste to fluid 20 being treated, is low cost, and/or has a reasonable battery lifetime. FIG. 1A implements the reactor 10 as a hand-held straw for purifying liquids, such as water, for human consumption. In such embodiments, the UV reactor 10 has long, thin tubes, straws or similar devices on each end of the reactor 10. In this embodiment, the straw may be a stainless steel tube 30 to absorb UV light at the inlet and outlet regions of the reactor 10, which may be important for safety reasons.

To start and stop the purification process, the reactor 10 may have one or more flow sensors (not shown) that detect flow through the reactor 10 and/or straw(s) to responsively control the output of one or more UV sources. Illustrative embodiments may be externally powered, contain rechargeable batteries, and/or capacitors that enable operation of the reactor 10 even when disconnected from an external power source.

Figure 1B:
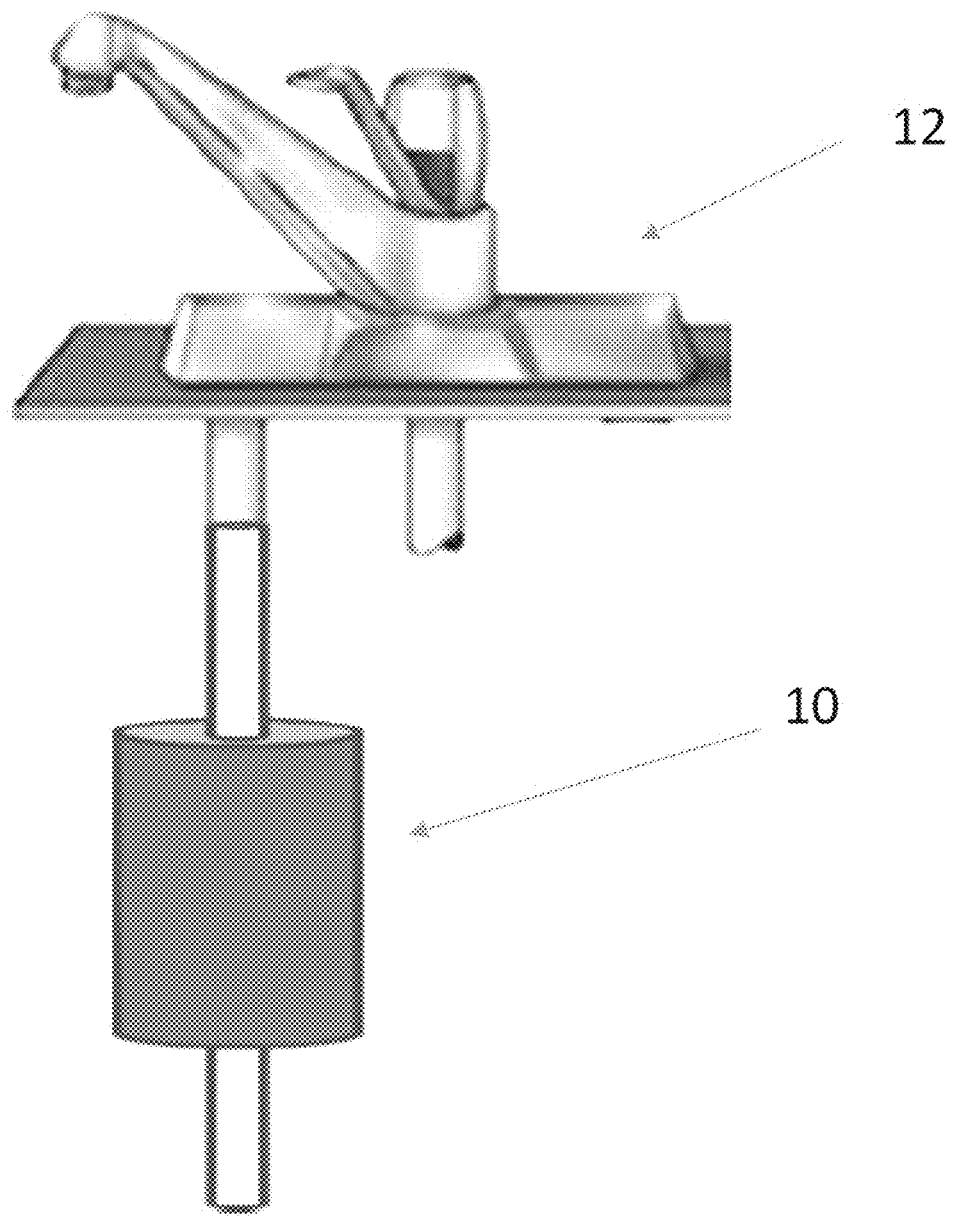
FIG. 1B schematically shows another use of the UV reactor of FIG. 1 in accordance with illustrative embodiments of the invention.

In other embodiments, the UV reactor 10 may be configured as a point-of-use module attached in-line with a source of fluid (e.g., drinking water in a kitchen faucet 12), as shown in FIG. 1B. Such embodiments may connect directly between the pipes directing water to or from the faucet 12. This embodiment, for example, shows the UV reactor 10 coupled serially to the path of a water inlet pipe. In some situations, it may be desirable to put multiple UV reactors 10 in series in order to achieve higher levels of disinfection or safety. This approach may be more attractive than a single large reactor due to the low cost of the small reactor 10 described in illustrative embodiments.

Illustrative embodiments disinfect the fluid by providing UV radiation from an LED. As described above, the LED may be triggered by a flow sensor that detects flow through the reactor 10. Additionally, or alternatively, the LED may be triggered on a preset schedule. The LEDs may pulse radiation in accordance with a variety of dosing schedules. U.S. Patent Application No. 62/891,503, which is incorporated herein by reference in its entirety, describes a variety of triggers and dosing schedules that may be used in accordance with illustrative embodiments of the invention.

FIGS. 2A-2G schematically show UV LEDs 100 configured in accordance with illustrative embodiments of the invention. As used herein, the term "LED" refers collectively to an LED chip 110 and a package 120. To the inventors' knowledge, there are two types of surface mounted UV LEDs 100. The first type of LED 100A (shown in FIGS. 2A-2B) includes the LED chip 110, the package 120 containing the LED chip 110, and a lens 130 (e.g., a quartz window 130) covering the LED chip 110 within the package 120. The second type of LED 100B (shown in FIGS. 2C-2G) includes an exposed LED chip 110 and a package 120 (e.g., a lidless package) containing the LED chip 110. The second type of LED 100B may be a commercially available device, such as the KLARAN™ UV LED, distributed by Crystal IS, Inc. and Asahi Kasei.

The UV LED chip 110, also referred to as the UV LED die 110, may be formed of a plurality of semiconductor layers 110A and 110B (e.g., sapphire on GaAlN). The two semiconductor layers 110A and 110B (see FIG. 2D) are shown for convenience only. A person of skill in the art understands that LED chips 110 may be formed of many more layers than those shown. In illustrative embodiments, the LED chip 110 is formed with an aluminum nitride (AlN) substrate having one or more quantum wells and/or strained layers, including AlN, gallium nitride (GaN), indium nitride (InN), or binary or tertiary alloy thereof. The LED chip 110 preferably has a substrate and/or device structure resembling those detailed in U.S. Pat. No. 7,638,346, filed on Aug. 14, 2006, U.S. Pat. No. 8,080,833, filed on Apr. 21, 2010, and/or U.S. Patent Application Publication No. 2014/0264263, filed on Mar. 13, 2014, the disclosures of which are incorporated herein, in their entireties, by reference. As known to those skilled in the art, the specific semiconductor materials and layer structure of the light emitting diode 100 may be selected so that a desired specific wavelength (or wavelength range) of light is emitted by the LED 100. Preferably, the LED chip 110 emits UV light having a peak wavelength range of 260 nm to 270 nm to provide effective, consistent treatment of fluid.

The LED chip 110 has a top radiation emission surface 150 from which UV light is emitted. However, while most of the UV light is emitted from the top surface 150 (also referred to as top light emitting surface 150), some smaller portion of the UV light may also be emitted by side surfaces 160 of the LED chip 110. Therefore, in illustrative embodiments, the top surface 150 is considered the primary light emitting portion and the side surfaces 160 may be considered non-primary light emitting portions of the LED 100.

To capture some of the side emitted light, some embodiments provide, on or in the package, a reflective inwardly facing surface 123 configured to reflect UV light emitted by the side surfaces 160. Reference to the "light emitting surface 150" and/or "light emission surface 150" is generally intended to refer to the primary light emitting portion of the LED. Furthermore, illustrative embodiments should not be interpreted as requiring a planar "surface" for the primary light emitting surface 150 of the LED, although some embodiments can have a planar surface for that purpose.

The bottom surface 170 of the LED chip 110 is electrically and thermally coupled with the top surface of the package 120. As known to those of skill in the art, the LED device 100 may include electrical contacts such as an anode 180 and a cathode 190. For example, as shown in FIG. 2C, the LED chip 110 may be mounted directly on the cathode 190. Such contacts may electrically couple to the chip 110 through the thickness of the package 120, e.g., using one or more vias or other connectors within the package 120.

Figure 2A:
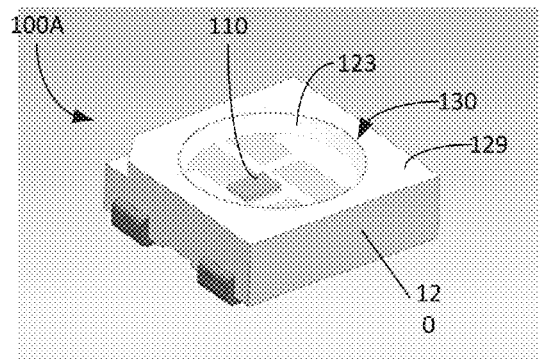
FIG. 2A schematically shows a perspective view of an LED in accordance with illustrative embodiments of the invention.
Figure 2B:
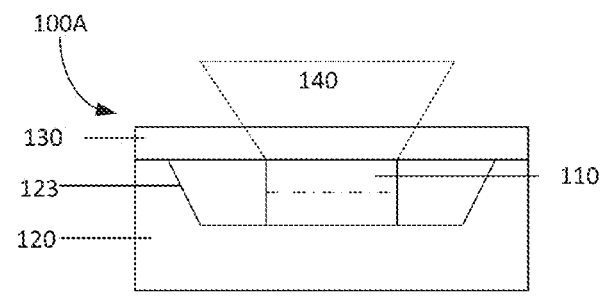
FIG. 2B schematically shows a cross-sectional view of the LED of FIG. 2A.
Figure 2C:
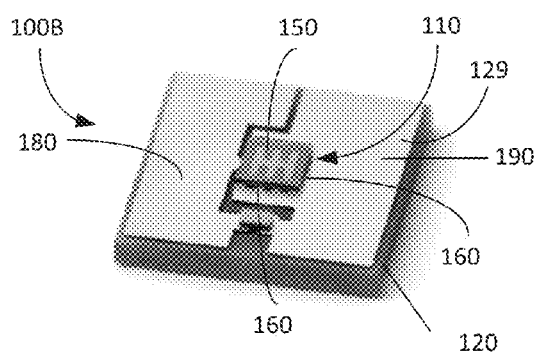
FIG. 2C schematically shows a perspective view of an alternative LED in accordance with illustrative embodiments of the invention.
Figure 2D:
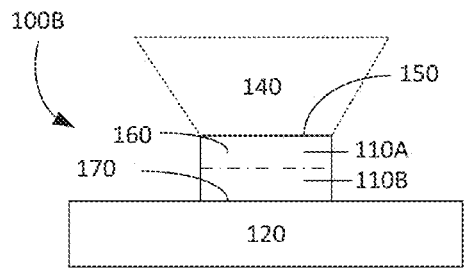
FIG. 2D schematically shows a cross-sectional view of the LED of FIG. 2C.
Figure 2E:
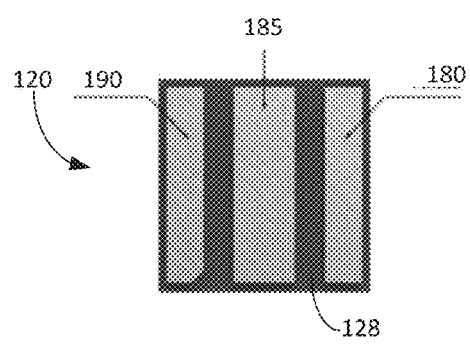
FIG. 2E schematically shows a bottom view of the LED of FIG. 2C.

FIG. 2E schematically shows a bottom surface 128 of the package 120, having the cathode 190, a thermal plate 185, and the anode 180. In use, the LED 100 is surface mounted on a printed circuit board (e.g., a flexible PCB). The LED 100 may be electrically coupled with the PCB 200 through the anode 180 and the cathode 190. Furthermore, to spread heat, the LED 100 may be conductively thermally coupled with the PCB 200 by means of above noted thermal plate 185. To augment the thermal plate 185, the package 120 preferably also has a thin form factor, and/or is made from a material having a low thermal resistance.

Figure 2F:
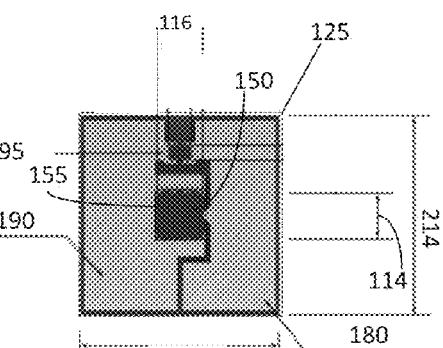
FIG. 2F schematically shows a side view of the LED of FIG. 2C.
Figure 2G:
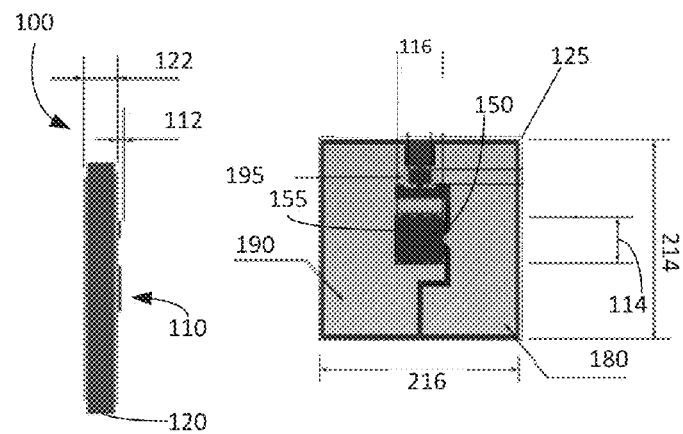
FIG. 2G schematically shows a top view of the LED of FIG. 2C.

FIGS. 2F and 2G schematically show side and top views of the LED 100 of FIG. 2E, respectively. In one implementation, the package 120 may have a thickness or height 122 of about 0.50 millimeters, a length 124 of about 3.50 millimeters, and a width 126 of about 3.50 millimeters. The LED chip 110 has dimensions that may be relatively small compared to the package 120. For example, the chip 110 may have a thickness or height 112 of about 0.11 millimeters, a length 114 of about 0.80 millimeters, and a width 116 of about 0.80 millimeters.

While the discussion of dimensions refers to LED 100B, it should be understood that illustrative embodiments are not limited to the dimensions described herein. Furthermore, the LED 100A may have the same or similar dimensions for the same or similar components.

The top surface 150 may define an area 155 or a perimeter 155. Generally, as noted above, the top surface 150 of an LED chip 110 may be substantially planar. However, illustrative embodiments may texture the top surface 150 and/or shape the top surface 150 in some other manner, such as in a "V" shape. Therefore, the top surface area 155 is intended to cover the area defined by the outer bounds and/or a perimeter of the top surface 150. In such an instance, the area 155 is not intended to be calculated by adding together the various portions that form the "top surface." For example, if the top surface 150 is a combination of two surfaces forming a "V" shape, the area 155 is the perimeter defined by the outer bounds of the "V" shaped top surface, and not the sum of the two separate surface areas. Accordingly, unless the context suggests otherwise, the area 155 is defined by the perimeter of the top surface 150.

Figure 3A:
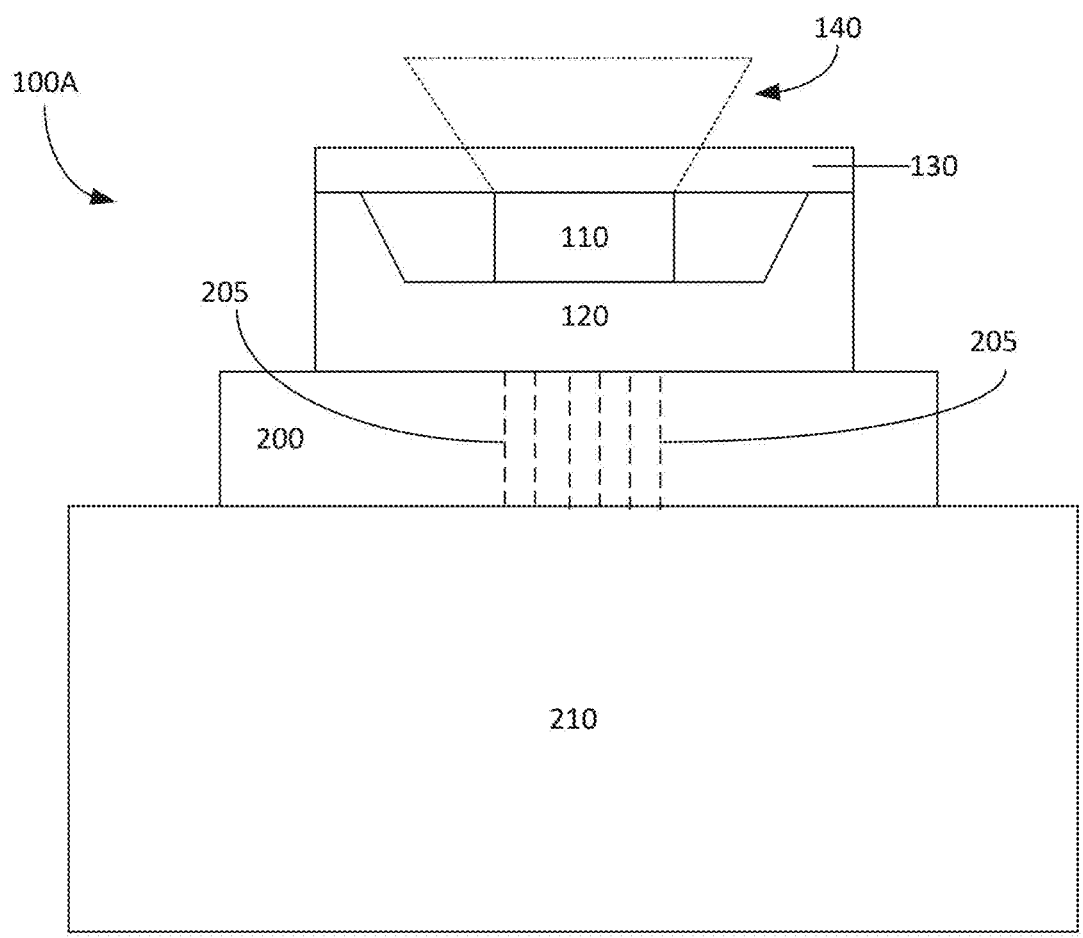
FIG. 3A schematically shows the LED of FIGS. 2A-2B mounted on a printed circuit board and a heat sink.

FIG. 3A schematically shows the LED 100A of FIGS. 2A-2B mounted on a printed circuit board 200 and a heat sink 210, in accordance with illustrative embodiments of the invention. When the LED 100A emits UV light (e.g., represented by cone of radiation 140), it can produce a considerable amount of heat. Undesirably, excess heat negatively impacts the light output and lifetime of the LED 100. Thus, proper thermal management preferably keeps the junction temperature (TJ) as low as is required for the given application and maintains the performance of the LED. The word "junction" refers to the p-n junction within the LED die 110, where the photons are generated and emitted. As shown in FIG. 3A, heat may be transferred away from this junction to the ambient by attaching the heat sink 210. To further assist with heat transfer, the PCB 200 may include thermal vias 205.

Figure 3B:
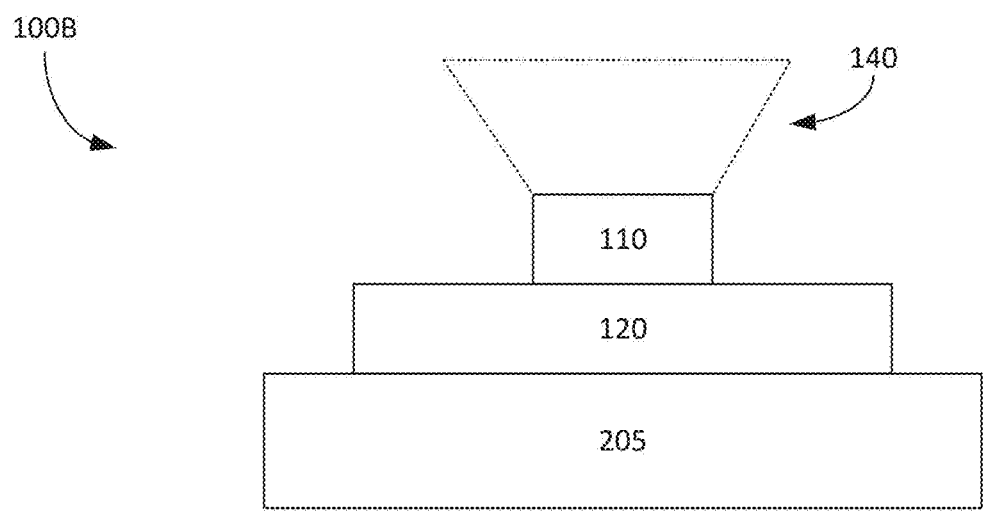
FIG. 3B schematically shows the LED of FIGS. 2C-2G mounted on a printed circuit board and a heat sink.
Figure 5:
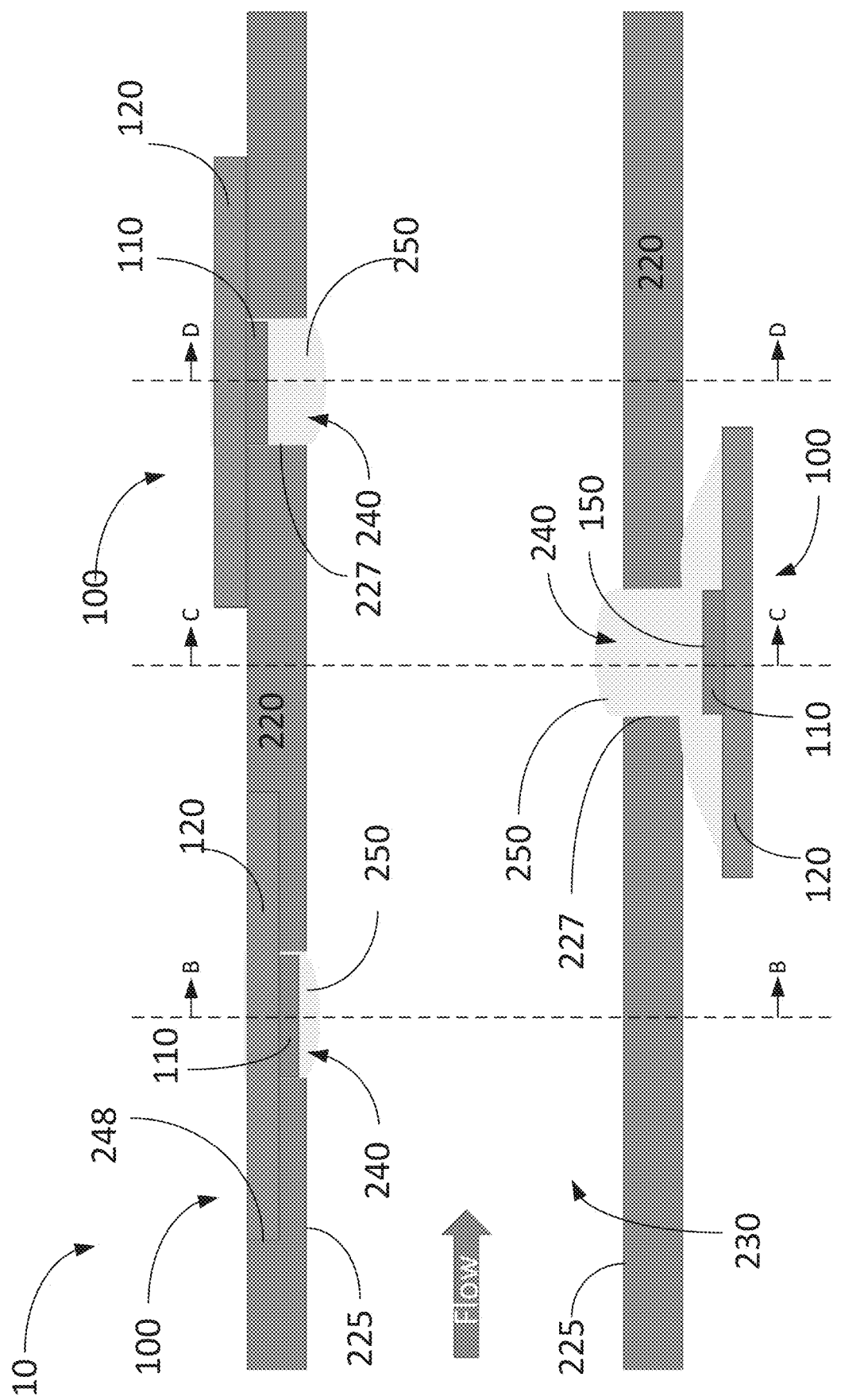
FIG. 5 schematically shows a sectional view of the UV reactor in accordance with illustrative embodiments of the invention.

FIG. 3B schematically shows the LED 100B of FIGS. 2C-2F mounted on the printed circuit board 200. In some embodiments, including that of FIG. 3A, the LED 100 is not coupled with the heat sink 210. Instead, because the LED chip 110 is exposed (e.g., the top light emitting surface 150 is not covered), illustrative embodiments may contact the LED chip 110 with an optical coupler having a low thermal resistance (as shown in FIG. 5, discussed below). The optical coupler draws heat away from the LED 100B, and allows for effective thermal management without the addition of the heat sink 210. Accordingly, some embodiments may have a considerably smaller form factor than may otherwise be available with the use of the heat sink 210. It should be understood, however, that some other embodiments may include the heat sink 210.

The figures schematically show the light emitting diode 100 on the substrate package 120. Among other things, this schematic drawing may represent one or more UV light emitting diodes 100, as well as supporting electronics, such as voltage regulators, avalanche breakdown diodes, silicon-controlled rectifiers, Zener diodes, and power sources. The package 120 may include one or more plastics, such as polyphthalamide (PPA) and/or one or more ceramics, such as aluminum nitride and/or alumina. In various embodiments, as noted above, one or more portions of a surface of the package 120 may be coated with a material reflective to UV light (e.g., aluminum or PTFE) and/or that is electrically and/or thermally conductive (e.g., one or more metals).

Figure 4:
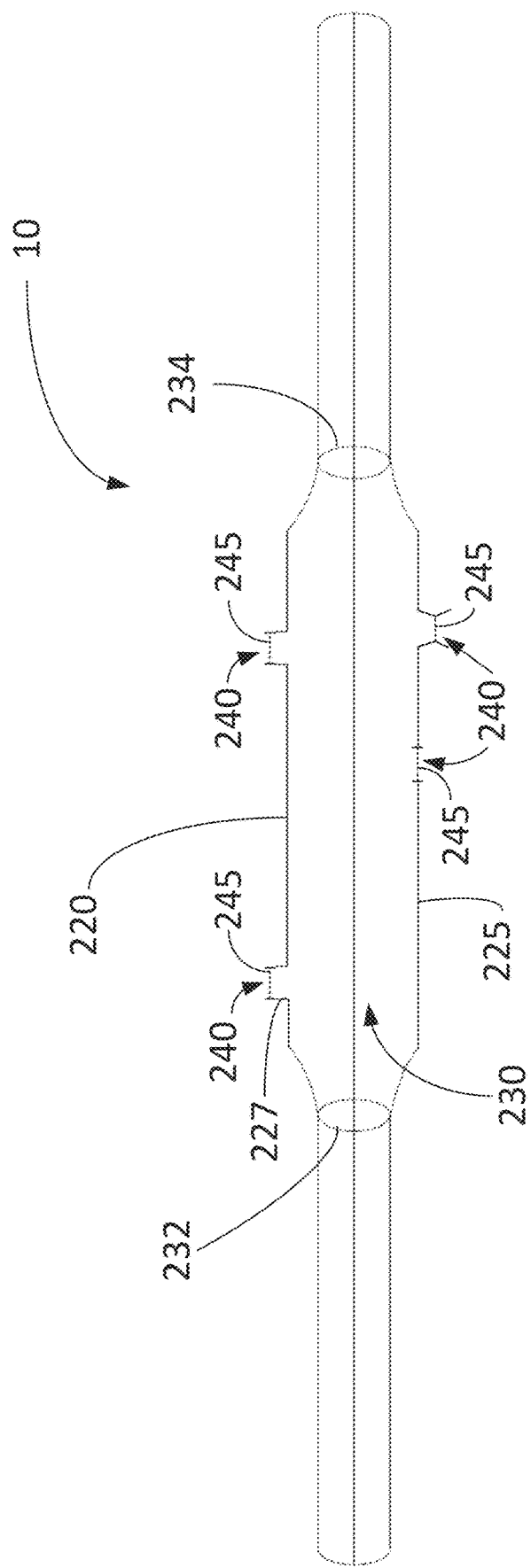
FIG. 4 schematically shows a UV reactor having apertures for receiving UV light into a chamber in accordance with illustrative embodiments of the invention.

FIG. 4 schematically shows the reactor 10 configured in accordance with illustrative embodiments of the invention. As shown, the chamber 230 has one or more apertures 240 for receiving light from a light source. The apertures may form an opening through the wall 220 of the chamber 230. Additionally, or alternatively, the aperture may form a bore extending outwardly from the chamber 230 (e.g., along a protruding portion from the chamber 230).

In illustrative embodiments, the light source is the LED 100, which is in optical communication with the light aperture 240. Specifically, the light emitting diode 100 may be secured to the body/wall 220 forming the chamber 230 using a variety of techniques. Those skilled in the art can select the appropriate securing technique. In some embodiments, the LED 100 may be thermally coupled with the wall 220. For example, solder material may be put on a top face 129 of the package 120.

As described previously, the light emitting diode 100 is selected to have a wavelength sufficient to reduce the level of contaminants or pathogens in the fluid being treated. For example, the wavelengths may be between about 200 nm and 320 nm. More precisely, the wavelengths may be between about 250 nm and 275 nm. Moreover, the UV light may be emitted from the primary light emitting surface 150 having an area 155. As discussed below, to optimize fluid treatment, some embodiments match the light aperture area 245 to the area 155.

FIG. 4 shows that the reactor 10 includes the wall 220, which defines the chamber 230 configured to contain fluid. Among other things, the fluid may be liquid water, although some embodiments contemplate more light absorbing liquids, such as fruit juices. Alternative embodiments may treat fluids in gaseous form. Accordingly, although much of this discussion relates to the reactor 10 treating liquids, such as water, those skilled in the art can apply various embodiments to other fluids.

During use, the fluid flows into the reactor chamber 230, via a fluid inlet 232, and exits the reactor chamber 230 after treatment, via a fluid outlet 234. Some embodiments may reverse the inlet and the outlet, enabling two-directional fluid treatment. As shown in cross-section in FIGS. 5 and 6A-6D, to facilitate fluid flow, the reactor 10 may have a generally curved arcuate inner surface forming a single wall. Indeed, the chamber 230 alternatively may have multiple internal walls and surfaces, and mechanical details (e.g., grooves, dimples, protrusions, etc.) to control flow of the fluid. The reactor chamber 230 may be formed from one or more materials compatible with the fluid to be treated, e.g., quartz, and the reactor chamber 230, or a portion thereof, may be substantially transparent to UV light.

To more effectively and uniformly treat fluids, the chamber 230 preferably is configured to reflect incoming UV light one or more times. To that end, the inner surface of the chamber 230 preferably is significantly reflective to UV light emitted into the chamber 230. Therefore, the inner surface 225, and an aperture wall 227, may be formed of a UV reflective material, and/or have a UV reflective coating. For example, the inner surface may reflect between 70 and 95 percent of incident UV light. Some embodiments may reflect more than 95 percent of incident UV light with certain treatments, such as aluminum coated with an appropriate dielectric layer or a multilayer Bragg reflector. To accomplish this, the inner surface may be coated with a material substantially reflective to the UV light, e.g., aluminum and/or polytetrafluoroethylene (also known as "PTFE"). For example, the multilayer Bragg reflector may achieve a reflectance of above 99%. Illustrative embodiments may have walls with reflectance of greater than 99%.

The coating may be diffusively reflective or specularly reflective, effectively confining the UV light within the reactor chamber 230. In various embodiments, the fluid is more effectively and uniformly treated via multiple interactions with the UV light caused by reflections from the sidewall 220 and/or the end surface. As such, appropriate inner surface reflectivity should be tuned to at least a minimum level of desired disinfection.

In general, the higher the reflectivity the better for small reactors 10. As the size of the reactor 10 increases and/or the absorption in the water increases, the advantage of reflectivity decreases (and making the walls 220 reflective may add cost to manufacturing). Thus, in some embodiments, when the reactor size is less than $1/\alpha$ or the reactor volume is less than $(1/\alpha)^3$ (where a is the absorption coefficient of the fluid and is equal to $-\ln(UVT)$ when measured in inverse centimeters), highly reflective walls 220 (with a large overall average reflectivity [R]) provide a substantial advantage. For highly transparent drinking water with a UVT of 98%, $1/\alpha$ is about 50 cm and decreases to about 10 cm for typical drinking water with a UVT of 90%. Impure water may have lower transparency. For instance, water with a UVT of 70% would have a $1/\alpha$ of about 3 cm.

In various embodiments, the UV reactor 10 is a flow-through reactor in which the fluid flows from the fluid inlet 232 to the fluid outlet 234 while being exposed to UV light reflecting about the chamber 230. In other embodiments, the UV reactor 10 is a batch reactor in which fluid is introduced into the reactor chamber 230, treated by UV light, and then extracted through the fluid outlet 234 after all or a portion of the illumination by UV light. As shown in FIG. 4, the chamber 230 may have a generally cylindrical shape that tapers towards the inlet 232 and the outlet 234. Thus, in addition to the sidewall 220 shown, it should be understood that a top and bottom endwalls, for example, may define the remainder of the chamber 230.

The wall 220 has one or more apertures 240 that allow UV light to enter the chamber 230 and disinfect the fluid therein. To improve the amount of light that is absorbed by the fluid and/or the microorganisms, the wall 220 may be formed from a UV reflective material (such as PTFE). Additionally, or alternatively, the inner surface 225 of the wall 220 may be formed from a UV reflective material and/or include a UV reflective coating. By forming the wall 220 and/or portions thereof from UV reflective material, the UV light reflects from the wall 220 rather than being absorbed by the wall.

Regular or larger sized UV reactors 10 may include a larger quantity of, and/or more powerful, LEDs 100. However, some embodiments are intended to be used as a small reactor, and therefore, have a smaller chamber 230. For example, illustrative embodiments may have a chamber 230 with a volume of about 90 cc. As the reactor 10 is made smaller, the area 245 of the aperture 240 becomes a larger total percentage of the total surface area of the chamber 230. Accordingly, with small reactors 10, the inventors discovered that making the aperture(s) 240 small with respect to the total chamber 230 surface area increases the average reflectivity in the chamber 230 and allows a higher dose of UV light for a given flow and given LED 100 input power.

Each of the apertures 240 has an aperture area 245. The aperture area 245 may be defined by a length and a width, a diameter, and/or a radius and angle, among other things. While illustrative embodiments provide various examples for defining the aperture area 245, it should be understood that the aperture 240 may take any shape, and is not limited to a rectangular, circular, or semi-circular cross-section. In some embodiments the aperture 240 area is defined by the smallest area of the aperture 240 (e.g., the smallest area 245 through which UVC radiation may escape the chamber 230 if the aperture 240 were not sealed and/or plugged). It should be understood by a person of skill in the art that the area 245 of the aperture 240 acts as an absorber (by letting light escape and/or not being reflective) compared to the total reflective area of the chamber 230. For example, in some embodiments, the aperture area 245 may be defined by the area at the end of the aperture 240 (e.g., in the case where the aperture extends out of the chamber 230 as in FIG. 4). Furthermore, in illustrative embodiments having multiple apertures 240, the total aperture area is the sum of the aperture area 245 of each individual aperture 240.

FIG. 5 schematically shows a reactor 10 having three apertures 240, and three LEDs 100. It should be understood that the orientation, positioning, configuration, and/or quantities of LEDs 100 is not intended to limit illustrative embodiments of the invention. Instead, the schematic orientation, positioning, configuration, and/or quantities of LEDs 100 is merely intended to describe examples of how illustrative embodiments of the invention may be implemented.

In illustrative embodiments, at least one, and preferably each, of the apertures 240 have an aperture area 245 that is smaller than a top surface area 125 of the package 120. In some other embodiments, the length and/or diameter of the aperture 240 is smaller than the length 124 of the package 120. Additionally, or alternatively, the width and/or diameter of the aperture 240 (as measured as its smallest point) is smaller than the width 126 of the package 120. Additionally, in some embodiments, the aperture 240 may have a package-fit portion 248 configured to fit the package 120 therein. In such instances, for example, the aperture area 245 is defined by its smallest area.

As shown in FIG. 5, in some embodiments, the aperture 240 is configured to fit the LED chip 110 therein. In some embodiments, the aperture 240 may be sized to be approximately the same size, or slightly larger, than the size of the LED chip 110. In some embodiments, the chip 110 of the LED 100B may be configured to fit within the aperture 240. Thus, the aperture area 245 may be sized to match the area 155 of the exposed top radiation emission surface 150. To that end, in some embodiments, the aperture area 245 is defined by a length and a width of less than about 1 millimeter by about 1 millimeter. For example, the aperture 240 has a length of about 0.8 millimeters. Additionally, or alternatively, the aperture 240 may have a width of about 0.8 millimeters. When the LED 100A is the type having a lens 130 covering the chip 110, the aperture 240 may again be sized to fit the chip 110. In some embodiments, the aperture area 245 may be sized to be smaller than the area of the package 120, but larger than (or approximately equal to) the area 155 of the chip 110. Yet in further embodiments, the aperture area 245 may be smaller than the surface area 155 of top surface 150.

To more effectively couple the UV light into the chamber 230, various embodiments employ an optical coupler 250 between the light emitting diode 100 and the chamber 230 as shown in FIGS. 5-6F. As discussed previously, the optical coupler 250 may serve as a barrier between the light emitting diode 100 and the chamber 230 and at least partially fluidly seals 280 the light aperture 240. Importantly, the optical coupler 250 preferably has an index of refraction that is greater than the fluid in the reactor. For water, the index of refraction is approximately 1.36 (between 1.35 and 1.37) in the preferred wavelength range of the UVC LEDs 100 used for disinfection (225 nm to 300 nm, preferably 265 nm). Aluminum nitride (AlN) has an index of refraction of 2.3 to 2.6 in the same wavelength range with an index of refraction of about 2.5 at the preferred wavelength of 265 nm.

In illustrative embodiments, the optical coupler 250 preferably has an index of refraction that is greater than the fluid (e.g., water), but less than or approximately equal to that of the semiconductor (e.g., AlN). Silicone, for example, has an index of refraction that is around or greater than 1.5. Polytetrafluoroethylene has an index of refraction around 1.3 to 1.4 which is also satisfactory although a larger index of refraction would typically be preferred. However, while less efficient, some embodiments may use an optical coupler 250 having an index of refraction greater than the semiconductor. Alternatively, some embodiments may use an optical coupler 250 having an index of refraction less than the fluid. Regardless of the index of refraction, the optical coupler 250 is preferably substantially transparent to UV light (preferably UVC light). Accordingly, the optical coupler 250 helps bring the UV light into the chamber 230 as noted above.

In some embodiments, the optical coupler 250 is greater than 99%, 95%, 90%, 85%, 80%, 75%, or 70% transparent to UV light. The optical coupler 250 may be greater than 50% transparent to UV light. However, at lower UV transparencies (such as 50%) the optical coupler 250 absorbs much of the UVC radiation. The inventors discovered that lower UV transparency optical couplers 250 degrade with time, and therefore, make the seal 285 unreliable. Therefore, in preferred embodiments, the optical coupler 250 has greater than 80% UVC transparency (e.g., the optical coupler is UV resistant).

In illustrative embodiments, the optical coupler 250 does not significantly degrade over time and/or under prolonged UVC exposure. To facilitate manufacturability and functionality, the optical coupler 250 preferably is produced from a moldable and mechanically stable material. For example, the optical coupler 250 may be formed from optically transparent polytetrafluoroethylene, such as a CYTOP amorphous fluoropolymer, distributed by AGC Americas. As another example, the moldable member may be formed from silicone material having the desired qualities.

The interface of the optical coupler 250 to the inside of the chamber 230 may be specially shaped to optimize light transmission and/or heat transmission (discussed below). For example, the top of the optical coupler 250 of FIG. 5 has a generally convex shape that enables more photons from the light emitting diode 100 to pass through the optical coupler at a substantially perpendicular angle. This should enable more photons to enter the chamber 230, desirably enhancing fluid treatment.

Rather than securing a relatively large and expensive heat sink 210 to the backside of the light emitting diode 100, the inventors recognize that they could configure the optical coupler 250 to also act as a heat pipe. Specifically, the optical coupler 250 preferably is selected to have a prescribed thermal conductivity that directs heat from the light emitting diode 100 and into the chamber 230. This configuration beneficially uses the fluid being treated as a coolant to remove heat from the light emitting diode 100, eliminating the need for an expensive heat sink.

Although FIG. 5 shows that the LEDs 100 are covered by the optical coupler 250, some embodiments do not include the optical coupler 250. For example, the LED 100 positioned in the package fit portion 248 may not use the optical coupler 250. Thus, in some embodiments, the chip surface 150 can be exposed to the fluid. In embodiments with no optical coupler 250 sealing the aperture 240, the package 120 preferably is sealed to the wall (e.g., portion 248) so that no fluid/water escapes back to the electrical connection. In some embodiments, direct contact of the chip 110 with the water may assist with thermal management.

FIGS. 6A-6F schematically show cross-sections of various configurations of the UV reactor 10.

Figures 6A, 6B:
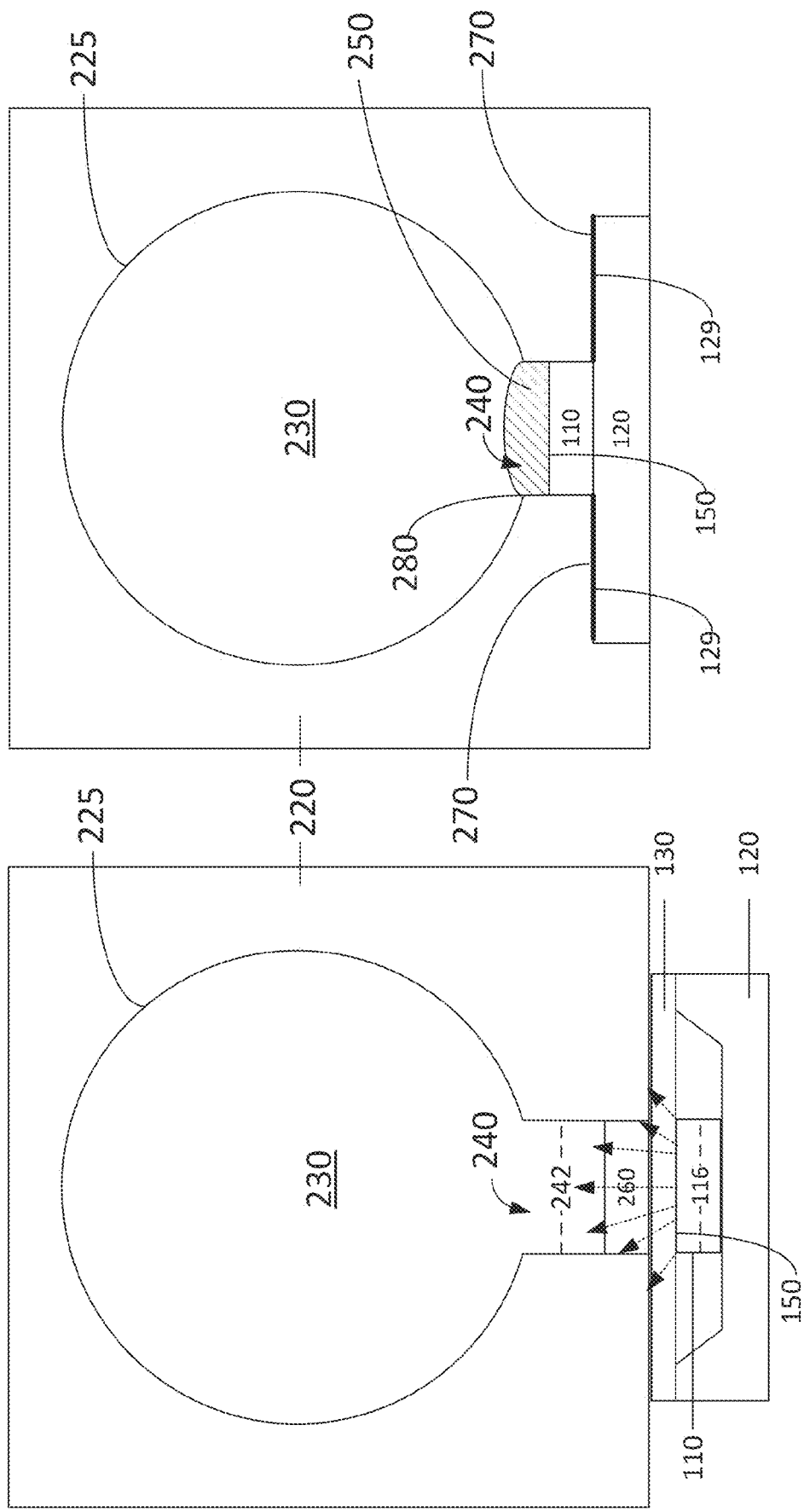
FIG. 6A schematically shows a cross-sectional view of the UV reactor having an LED transmitting light into the chamber through an aperture in accordance with illustrative embodiments of the invention.
FIG. 6B schematically shows a cross-section along line B-B of FIG. 5.

FIG. 6A schematically shows a cross-section of the UV reactor 10. As shown in the figure, the chamber 230 has a generally circular cross-section. However, the chamber 230 may have any of a variety of shapes, including a rectangular cross-section.

The chamber 230 has at least one aperture 240 having an aperture area 245. In illustrative embodiments, the aperture area 245 is approximately the same size as the LED chip top surface area 155. For example, if the aperture 240 is cylindrical, the aperture diameter 242 may be approximately the same as the length 114 and width 116 of the chip 110. Alternatively, if the aperture 240 cross-section is rectangular, the length and width of the aperture area 245 may be approximately the same as the length 114 and width 116 of the chip 110, respectively.

In illustrative embodiments, the LED 100 may be placed directly up against the opening of the aperture 240. In some embodiments, the aperture 240 may have a sealing member 260 to prevent fluid from escaping the chamber 230. The sealing member 260 may be, for example, a quartz window. Alternatively, the sealing member 260 may be the optical coupler 250. Preferably, the sealing member 260 is UV transparent. Some embodiments may have the optical coupler 250 coupled with the LED 100 and with a separate sealing member 260 (e.g., a quartz window).

In various embodiments of the invention, the optical coupler 250 may be silicone-based, and may be formed from, for example, Deep UV-200 available from Schott North America, Inc. of Elmsford, N.Y., or a similar material. In other embodiments, the optical coupler 250 may be formed from a fluorinated polymer such as polytetrafluoroethylene (PTFE), e.g., Optical PTFE available from Berghof Fluoroplastic Technology GmbH of Eningen, Germany, or Teflon AF available from DuPont, or Cytop (a polymerized perfluoro(4-vinyloxy-1-butene), available from Asahi Glass company. In various embodiments, the optical coupler 250 may be formed from a silica-based polymer.

As shown in FIG. 6A, the lens 130 (e.g., quartz window) may be placed against the opening of the aperture 240. The thickness of the lens 130 may cause the radiation emission surface 150 to be further away from the opening of the aperture 240 than it might otherwise be if the chip 110 were placed directly against the opening of, or into, the aperture 240. Thus, when the LED is powered on, light is emitted (e.g., in a generally conical pattern 140), such that some of the light (represented by dashed-lined arrows) may not enter the aperture 240. The light that does not enter the aperture is unlikely to make it into the chamber 230 to disinfect the fluid.

In various embodiments, the top surface 155 of the LED chip 110 may be less than 5 millimeters away from the opening of the aperture 240. Preferably, the LED chip 110 may be less than 1 mm away from the opening of the aperture 240. However, this may be difficult to achieve, as the thinnest windows 130 currently made are about 0.25 mm thick. However, illustrative embodiments using the LED 110B may be position the chip 110 less than 11 mm away from the opening of the aperture 240, and preferably less than 0.25 mm.

FIG. 6B schematically shows a cross-section of another LED 100 configuration along line B-B of FIG. 5. As shown, the light emitting diode 100 fits into a recess and may be sealed with a material, such as silicone, at its edges, while using the optical coupler 250 in a much more focused manner than in FIG. 6A. Illustrative embodiments may include an LED 100 without the lens 130. Instead, the optical coupler 250 may be intimately coupled with the LED chip 110. The inventors discovered that this configuration provides a number of advantages.

As described previously, the optical coupler 250 increases the total amount of light emitted from the emission surface 150 of the LED chip 110. Eventually, the optical coupler 250 interfaces with the fluid (e.g., air or water) in the chamber 230. While in some embodiments the optical coupler 250 may have an index of refraction that is about the same as the semiconductor chip 110, illustrative embodiments still provide increased total light emission relative to prior art LEDs that do not use the optical coupler (and instead use other components such as lens 130, window 260, and/or no additional components).

The total amount of light that reaches the fluid in the chamber 230 is increased because the optical coupler 250 removes the semiconductor-air interface. Without the optical coupler 250 the semiconductor chip 110 interface is air (e.g., because the chip 110 is not intimately coupled with the lens 130 and/or quartz window 260, and air exists between the chip 110 and the lens 130 and/or window 260). The transition of interfaces may be therefore considered to be, for example, (a) semiconductor chip 110 to air, (b) air to lens 130, (c) lens to air, (d) air to quartz window 260, and (e) quartz window 260 to fluid in the chamber 230. Even for an unlidded type LED 100B, the transition of interfaces may be, for example, (a) semiconductor chip 110 to air, (b) air to quartz window 260, (c) quartz window 260 to fluid in the chamber 230. Therefore, in some embodiments, the optical coupler 250 eliminates the air interface at the chip 110 surface, leaving only, for example, (a) semiconductor to optical coupler, and (b) optical coupler to fluid in the chamber. Thus, in some other embodiments, the optical coupler 250 eliminates the air interface at the chip 110 surface and/or the lens 130 top surface (e.g., between lens 130 and window 260 in FIG. 6A). Therefore, the optical coupler 250 may advantageously eliminate the (a) semiconductor chip 110 to air interface, (b) air to lens 130 interface, (c) lens 130 to air interface, and/or (d) the air to window 260 interface.

Accordingly, the optical coupler 250 may provide fewer interface transitions (during which otherwise light may be totally internally reflected and lost prior to entering the chamber 230). Because water has an index of refraction that is substantially greater than that of air, the elimination of the semiconductor to air interface greatly increases the amount of UVC radiation emitted into the water (or other fluid with similar values for the index of refraction).

As an additional advantage, the distal end 285 of the optical coupler 250 may be convexly shaped, and thus more of the light escapes. Furthermore, the optical coupler 250, which may have an index of refraction of about the same as the semiconductor, or less, is in direct intimate contact with the fluid in the chamber 230 (e.g., water) instead of air. The optical coupler 250 may further advantageously form the fluid seal 280 with the chamber, thereby eliminating the need for another material to cover the LED 100. These advantages are discussed in further detail below.

For the reasons described above, the inventors believe that total light emission increases because the optical coupler 250 has an index of refraction that is greater than air, thereby reducing index of refraction mismatches that may otherwise occur (e.g., as opposed to direct contact of the semiconductor surface 150 with ambient air and/or fluid). This reduces the likelihood that light internally reflects from the surface 150 interface. The optical coupler 250 decreases the critical angle (i.e., the angle at which light does not escape from the semiconductor surface 150 due to total internal reflection), thereby allowing more light to escape from the chip 110 surface 150.

To reiterate, the inventors also discovered that the optical coupler 250 further increases the total amount of light that is emitted by the LED 100 by intimately coupling the optical coupler 250 with the light emitting surface 150. To be in intimate contact, the atoms of the optical coupler 250 are within a quarter of a wavelength distance away from the atoms of the light emitting surface 150. Intimate contact between the optical coupler 250 and the surface 150 further reduces the amount of light that is reflected back towards the surface 150 due to total internal reflection for light that is outside the escape cone and reflected light within the escape cone due to the index of refraction mismatch.

For UVC wavelengths of around 250 nanometers, intimate contact with the emission surface 150 can be difficult to accomplish. For example, illustrative embodiments having the quartz window 130 (e.g., shown in FIG. 6A) are generally unable to intimately contact the LED chip surface 150. However, in illustrative embodiments the optical coupler 250 is in intimate contact with the surface 150. The optical coupler 250 may be in a generally moldable and/or fluid form when initially contacting the chip 110. After contact, the optical coupler 250 may then be cured into a hardened or solid phase. In illustrative embodiments that cure the optical coupler 250 (e.g., to form the seal 280), the optical coupler 250 is formed of a material that maintains intimate contact after curing. Thus, during manufacturing, the LED chip 110 may be "pressed" into the optical coupler 250 while the optical coupler 250 is "soft," thereby intimately coupling the chip 110 with the optical coupler 250.

Another advantage of illustrative embodiments includes that the optical coupler 250 may form a fluid tight seal 280 with the chamber 230. Thus, the sealing member 260 may be eliminated from the UV reactor 10, thereby simplifying manufacturing. As an additional advantage, in some embodiments, removing the sealing member 260 may assist with preventing additional reflection (e.g., caused by the transition of light from lens 130 to sealing member 260 in FIG. 6A). However, in some embodiments, the optical coupler 250 may be positioned between, and intimately coupled with, the LED chip 110 and the sealing member 260.

Illustrative embodiments advantageously form the optical coupler 250 from a heat conductive material, such as sapphire. Sapphire has a thermal conductivity of 35 W/m-K and can be affixed to the surface 150 of the LED die with a very thin layer silicone to minimize the thermal resistance. If the optical coupler 250 is formed from sapphire, has a thickness of 0.4 mm, and a length and width to match the die 110 surface (e.g., area approximately equal to 1 mm$^2$) than the thermal conductivity of the optical coupler can be as high as 0.14 W/K. The fluid in the chamber 230 may cool the optical coupler 250 as it conducts heat from the LED 100. Therefore, illustrative embodiments reduce cool the diodes 100 out their top surface 150 (the same surface used for emission of UVC radiation) rather than requiring more expensive and bulkier heat sinks 210 for the back of the LED 100 (where the electrical connections are located). To further enhance heat transfer from the LED 100 into the chamber 230, some embodiments may thermally couple the wall 220 using a conductive thermal material 270 (e.g., solder material) on a top face 129 of the package 120. The thermally conductive material may help conduct additional heat away from the LED 100 towards the fluid in the chamber 230.

For example, a commercially available Klaran™ diode rated to produce 65 mW of output UVC power produces 4 W of heat when operating at the rated current of 500 mA. Under these conditions, the optical coupler 250 formed from sapphire allows a temperature rise across it of only 29 K. Since Klaran™ have a typical thermal derating of 0.5%/K, this represents a drop in output power of 15%, which is acceptable in some embodiments and comparable to what is achieved with most heat sinks 210.

Another approach to heat sinking the LED diode 120 is to use copper (Cu) strips, which have a thermal conductivity of 385 W/m-K. For example, for the LED shown in FIG. 2C, two strips of Cu foil can be attached to the front surface of the LED 120 using a thermal grease and/or a thermal epoxy to make good thermal contact. One strip attaches to the anode 180 side of the LED die 110 and the other strip may attach to the cathode 190 side of the LED die 110. The total area contacted this is approximately 6 mm$^2$ (e.g., two strips which are each 3 mm$^2$ in size). The thickness of the Cu is more than the LED die 110. For example, 0.4 mm could be used. Thus, the Cu strips provide a thermal path with a conductance of $(385 \text{ W/m-K}) \times (6 \times 10^{-6} \text{ m}^2)/(0.4 \times 10^{-3} \text{ m}) = 5.8 \text{ W/K}$. A commercially available Klaran™ diode rated to produce 65 mW of output UVC power produces about 4 W of heat when operating at the rated current of 500 mA.

Under these conditions, the Cu strips allow a temperature rise across them of about 0.7 K. The temperature difference between the LED die 110 and the Cu strips is kept small by the high conductivity of the LED package 120 which, for Klaran™ is made from AN ceramic. The Cu strips may be attached to the window material 260 covering the aperture 240. The window may be cooled by direct contact with the fluid. Because the window material 260 is relatively large in area, the thermal drop across it is quite small (for instance, a 5 mm dia. sapphire window that is 0.25 mm thick has a thermal conductivity of about 2.7 W/K and a temperature rise of 1.5 K when 4 W of heat are driven across it). Thus, the LED die 110 sees a temperature rise of 2.2 K, which is negligible. This heat sinking may prove advantageous in reducing costs of manufacturing and bill of materials.

Figure 6D:
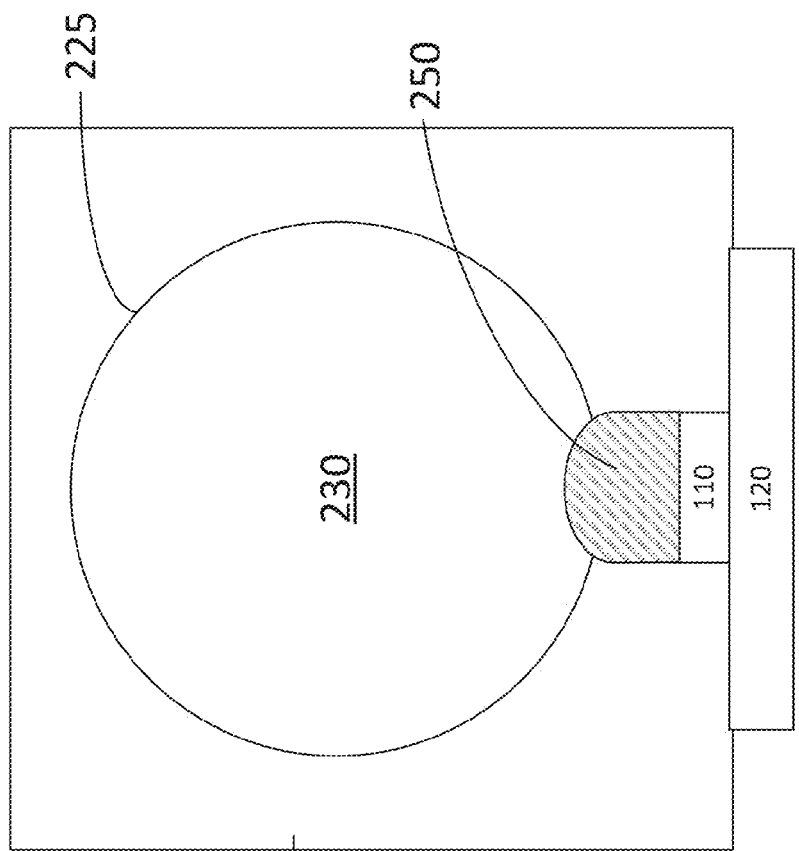
FIG. 6D schematically shows a cross-section along line D-D of FIG. 5.
Figure 6C:
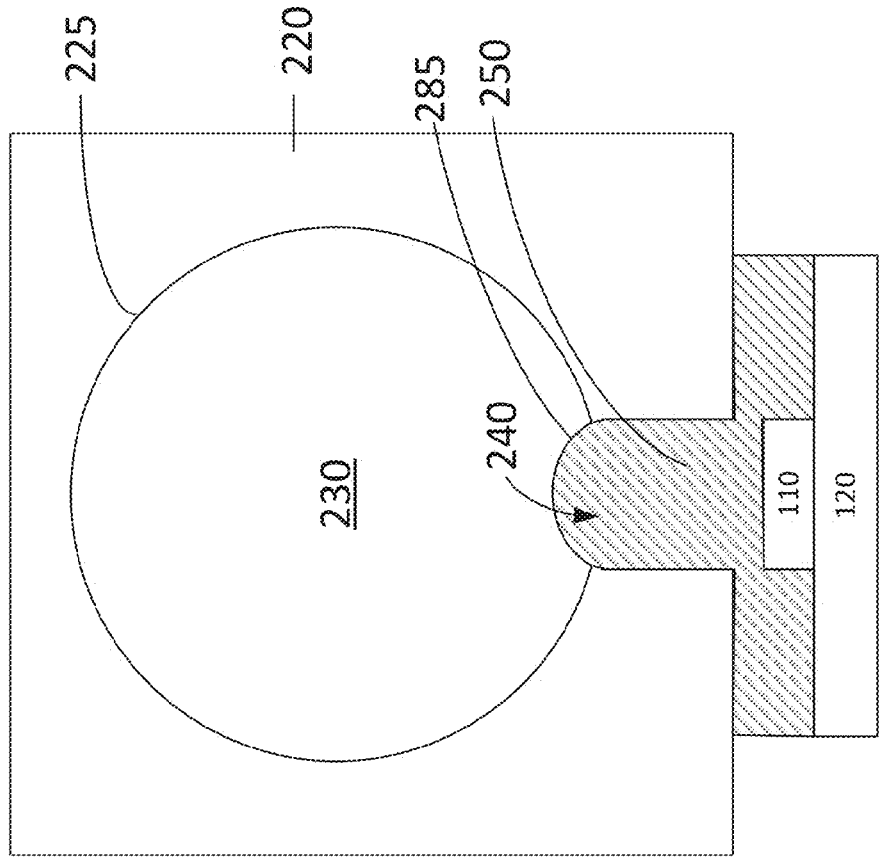
FIG. 6C schematically shows a cross-section along line C-C of FIG. 5.

FIG. 6C schematically shows a cross-section along line C-C of FIG. 5. As shown, the LED chip 110 is not within the aperture 240. Instead, the chip 110 is a distance from aperture 240. Similar to FIG. 6B, the optical coupler 250 is positioned between the chip 110 and the chamber 230. Additionally, the optical coupler 250 may have a distal portion 285 having a convex shape. The convexly shaped distal portion 285 allows more light to escape from the optical coupler 250 into the chamber 230. Additionally, or alternatively, the distal portion 285 may be textured/roughened to assist with photon transmittance into the chamber 230. Although FIG. 6C shows that the distal portion 285 is convex, it should be understood that the distal portion may take a variety of shapes (e.g., a flat shape). The distal portion 285 may be textured to assist with emitting light.

FIG. 6D schematically shows a cross-section of another LED configuration along line C-C of FIG. 4. The configuration in FIG. 6D is similar to the configuration in FIG. 6B, except the wall 220 does not have a package receiving portion.

FIG. 6E schematically shows yet another LED 100 configuration in accordance with illustrative embodiments. As can be seen, the LED 100A is of the type having a lens 130. However, illustrative embodiments may also use the unlidded type LED 100B. The aperture 240 is larger than the radiation emission surface area 155 and smaller than the perimeter of the package 120. A larger aperture area 245 may be advantageous when the chip 110 is not positioned directly in or adjacent to the aperture 240, thereby allowing more of the emitted light to enter the aperture.

FIG. 6F schematically shows yet another LED 100 configuration in accordance with illustrative embodiments. FIG. 6F schematically shows the light emitting diode 100 connected to the body of the reactor 10 in accordance with other embodiments of the invention. This embodiment also shows spring-loaded contacts 290 for receiving power.

As shown, in some embodiments the aperture area 245 may be smaller the top surface area 155. Whereas prior art aperture areas 245 are generally made quite large to maximize the amount of UV light that enters the chamber 230, the inventors recognized that larger aperture areas 245 undesirably allow more light to leave the chamber 230. For example, some prior art light apertures known to the inventors may take up to 30-50 percent of the total surface area of the chamber 230. This is especially true for small reactors 10, where the total light entering the chamber is relatively low to begin with. Therefore, because the aperture area 245 is small, less light escapes the chamber 230. So long as the inner surface 225 is sufficiently reflective, the small aperture 240 results in more of the light being absorbed by the fluid and the pathogens therein.

Accordingly, illustrative embodiments of the invention minimize the size of the light aperture 240 relative to the overall surface area of the interior walls 225 of the chamber 230. In illustrative embodiments, the light aperture 240 size is minimized, but the UV reactor 10 is configured such that substantially all of the light photons from the light emitting diode 100 enter the chamber 230. In other words, the numerical aperture, which is a measure of amount of light that transmits through the light aperture 240 relative to the light emitted, preferably is close to unity. In some embodiments, the light aperture 240 size is reduced, but the UV reactor 10 is configured such that at least 80% of the UV light to enter the chamber. Furthermore, in some embodiments the light aperture 240 size is further reduced, and the UV reactor 10 is configured such that at least 60% of the total UV light output to enter the chamber 230.

For example, the area 245 formed by the light aperture 240 may take up no more than 1 to 25 percent (e.g., no more than 17%) of the total combined surface area of the reflective walls 220 and the aperture area 245. In various embodiments, the aperture area 245 is about the same as the surface area of the light emitting portion 150 of the light emitting diode 100. Such embodiments may also size the light aperture 240 to be larger than the surface area 155 of the chip 110.

For example, for a small reactor having a 100 cm$^3$ chamber volume, the surface area may be roughly 22 cm$^2$ or more. For an aperture area of 1 mm$^2$ (0.01 cm$^2$), the aperture is less than about 0.05% of the area.

Although various figures have shown the optical coupler 250 positioned in the chamber 230, it should be understood that in some embodiments the optical coupler does not extend into the chamber 230. For example, as shown in FIG. 6F, in some embodiments, the optical coupler 250 is positioned in and forms the seal 280 with the aperture 240. In some embodiments, however, the optical coupler 250 does not form the seal 280 with the aperture 240.

Those skilled in the art may position the LED 100 at least partially within the light aperture 240, or external to the light aperture 240. Moreover, some embodiments may minimize the size and geometry of the aperture area to be smaller than the chip 110 area 155. Specifically, some embodiments may use light pipes or similar technologies to direct the light into a more concentrated region. U.S. provisional patent application No. 62/755,041, the disclosure of which is incorporated herein, in its entirety, by reference, describes light pipe and configurations that may be used in accordance with some embodiments. The light aperture 240 also may be tapered or otherwise shaped, with or without light pipes, to focus light into the chamber 230 in a desired manner.

A simple approximation of the dose (D) applied to a fluid, may be represented by Equation 1.

Dose delivery in a continuous-flow UV reactor is subject to hydrodynamic irregularities and a variable UV intensity distribution, and is a function of the UV absorbance of the water, the flowrate through the reactor, the UV output from the LED 100, and the hydraulic characteristics within the reactor 10. As such, it can be difficult to calculate directly UV dose within a UV reactor 10. If all microorganisms leaving the reactor 10 receive the same dose, the reactor 10 is termed an "ideal" reactor. However, these ideal conditions do not generally exist in UV reactors 10. As such, microorganisms passing through the UV reactor 10 are exposed to different doses. The difference is UV doses experienced by microorganisms may be characterized by a dose distribution.

The dose distribution is the probability distribution of UV doses that microorganisms receive in the UV reactor 10 (e.g., represented by a histogram of UV dose mJ/cm$^2$ v. occurrence probability). Some microorganisms in the fluid travel close to areas where UV dosage is high while others may experience a lower dosage. Some microorganisms may travel through the reactor 10 quickly while others travel a more circuitous path. A narrow dose distribution is generally preferred and indicates more ideal hydrodynamic conditions. A wider dose distribution indicates less efficient reactor performance and results in a greater degree of "overdosing" to ensure that the minimum desired dose is achieved for the microorganisms at the lower end of the dose distribution.

To the inventors' knowledge, there are currently no convenient, accurate methods to measure directly the dose distribution in a continuous flow UV reactor 10, but mathematical models can help to characterize dose distribution. The UV dose in the UV reactor 10 may be estimated as the reduction equivalent dose (or RED). The RED is a calculated dose for a flow through the UV reactor 10 that is based on biodosimetry (i.e., measuring the level of inactivated microorganisms with a known UV dose-response). The RED may be set equal to the UV dose in a collimated beam test that achieve the same level of inactivation.

In other words, the RED provides a calculation of a UVC dosage, based on the achieved reduction in bacteria, as if the provided dosage had been equally distributed throughout the volume of the chamber 230. The RED may be represented by Equation 1 below.

$$RED \leq \frac{(1-e^{-\alpha[r]})P_c}{\alpha f(1-[R]e^{-\alpha[r]})} \quad \text{Equation 1}$$

Because of the non-uniformities in the chamber 230 the actual measured RED is always less than the calculated ideal, because the amount of pathogen deactivation is exponentially based on the UVC light the pathogen absorbs. Take the example where a certain dose provides a four-log reduction in active bacteria (factor of 10,000). If some part of the fluid is only receiving half of that dose, in that particular region, the effective pathogen reduction may be only a two-log reduction (e.g., reduced from a factor of 10,000 to a factor of 100). The region that has only a two-log reduction ends up dominating the measured effectiveness of the reactor 10. Therefore, it is unlikely that the actual performance will be better than the ideal situation, which assumes a uniform dose for all the fluid passing through the reactor.

Pc is the UVC power that makes it into the chamber 230 (i.e., through the aperture 240). Pc is not necessarily equivalent to the dose that the LED 100 is outputting. For example, after the generated light is out of the chip surface 150, the light has to go through window 130 to get into the chamber 230 (which may reflect off the window 130), the aperture 240 is small (and may not gather all the light—e.g., if radiation is being emitted at all different angles; unless the aperture 240 is very large compared to the size of the UVC LED; the light that is emitted at a large angle will miss the aperture 240). Illustrative embodiments increase Pc by using the optical coupler 250 to increase the UVC dose that LED 100 is outputting. Additionally, some embodiments increase Pc by minimizing reflectivity from the windows 130 and or sealing member 260 by removing these components and replacing them with the optical coupler 250.

Prior art known to the inventors increases the RED by increasing Pc. Specifically, the prior art accomplishes this by attempting to make the aperture 240 large to capture all of the emitted light. However, large apertures 240 take up a substantial portion of the inner surface area of the chamber 230 (e.g., to fit a large quartz window). Thus, to the inventors' knowledge, the state of the art indicates that making the aperture 240 small provides an overall reduction in RED, counter to illustrative embodiments. However, the inventors recognized that for very small sized reactors 10 (e.g., 100 cc or less, particularly about 10 cc or less), the aperture 240 is a bigger part of the total surface 225 area. Accordingly, the large apertures 240 for small reactors 10 cause a disproportionate large drop in RED by undesirably decreasing average reflectivity of the chamber [R].

R is the average UVC reflectivity of the walls 220 (i.e., inner surface area) of the chamber 230. Apertures 240 factor into the [R] part of the equation, as do the openings that define the inlet 232 and/or the outlet 234. The smaller aperture 240 increases the average reflectivity relative to a larger aperture 240. However, a chamber with no aperture, all else being the same, has a higher average [R]. This is because the aperture 240 is a non-reflective portion of the total surface area. Illustrative embodiments are configured to have a high average reflectivity and a sub-100 cc chamber 230 volume. For instance, if the walls of the reactor chamber have a reflectivity of 95% (which is achievable using aluminum surfaces or with properly prepared PTFE surfaces), then the [R] can be calculated approximately as $$[R] = (0.95) \times \left(1 - \frac{\text{total area of the apertures}}{\text{total surface area of inner surface of reactor}}\right).$$

The total surface area of inner surface of reactor includes the total area of the aperture in the numerator.

The coefficient α is a property of the fluid. Pathogens, dissolved chemicals, and particles, among other things, contribute to the absorption of light in the fluid. Thus, different fluids have different coefficients. Indeed, even different samples of water may have variance in this coefficient. The equation for α=4.605−ln(UVT). WT is ultraviolet transmission, which is measured by percentage of light that is transmitted (i.e., not absorbed) through 1 cm of the fluid. The UVT value is expressed as a number that is less than 100. For example, if UVT were 98%, the coefficient is calculated as 4.605−ln(98)=0.020. If the fluid were completely transparent (UVT=100%), a would equal 0. Generally, drinking water has a UVT of about 96% to about 98% in the wavelength range around 265 nm, while wastewater or fruit juices can be much lower.

It is useful to define a figure of merit (FOM) for the reactor 10 designed to disinfect a fluid with an absorption coefficient of a (at the peak wavelength of the LEDs 100), such that $$FOM = RED \times \frac{\alpha f}{P_C}.$$

In theory, the best the reactor 100 could do is to have a FOM of unity (1). For small reactors 10 where the effective reflectivity [R] of the reactor chamber 230 is less than unity, the highest possible FOM is given by the equation:

$$FOM = \frac{1-e^{-\alpha[r]}}{1-[R]e^{-\alpha[r]}}$$

For large reactors where [r] is much larger than 1/α, the FOM is close to unity. However, for small reactors 10, particularly when the average reactor 10 dimension [r] is less than 1/α, then the FOM drops very rapidly for [R] less than unity.

Figure 7:
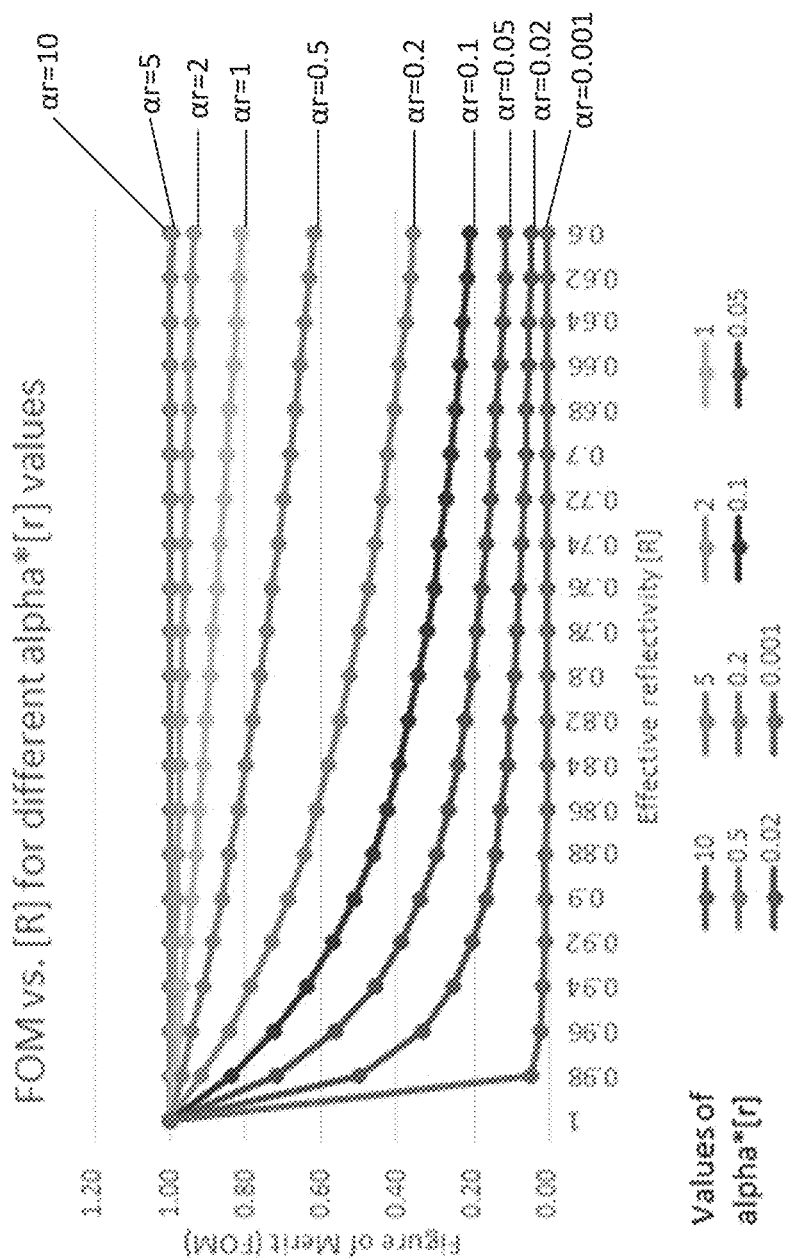
FIG. 7 schematically shows a plot of the FOM versus [R] for different values of α[r] in accordance with illustrative embodiments of the invention.

FIG. 7 schematically shows a plot of the FOM versus [R] for different values of α[r] is shown below. The FOM value correlates to how much of the UV light is absorbed by the fluid and/or particles therein. Thus, the FOM value is a measure of the quality of disinfection within the chamber 230 (i.e., generally the higher the FOM the better disinfection). The quantity α[r] is a function of the fluid and the size of the chamber 230. The average reflectivity [R] is defined to be the average reflectivity R of the chamber 230 where R varies with position on the chamber wall. As described earlier, the aperture 240 has 0 (or low) reflectivity when accounted for in the average reflectivity [R]. (For ease of convenience, the square brackets [ ] are used to represent average quantities.) Thus, as the size of the reactor 10 becomes smaller, a similarly sized aperture 240 takes up a larger and larger percentage of the total area of the chamber 230, causing the average reflectivity [R] to drop.

Drinking water typically has a UVT greater than 90% which means that a is smaller than $0.105\ cm^{-1}$. That means that the product α[r] drops from a little greater than 1 to less than 0.06 as the average dimension of the reactor, [r], shrinks from 10 cm to 0.5 cm. As α[r] drops below 0.5, the effect of the [R] on the FOM (and the resultant efficiency of the reactor) becomes enormous. Thus, in illustrative embodiments the small reactor 10 has a large [R] value to remain efficient. The large [R] value means that the percentage of the total area taken up by the aperture area 245 is little.

In an ideal case, RED may be represented by Equation 2. Note that this approximation ignores the effect of absorption in the fluid, which is appropriate for small reactors where the dimensions of the reactor 10 are much smaller than the absorption lengths in the fluid being disinfected (e.g., drinking water).

$$\text{RED} \le [r] * P_c/f(1-[R]), \text{where} \qquad \text{Equation 2:}$$

[r] is the average distance the emitted light/radiation travels before striking a wall (e.g., the average cross section of the reactor 10), Pc is the power from the light emitting diode 100 coupled into the reactor 10, f is the liquid flow rate (volume per unit time), and

[R] is the average UVC reflectivity of the walls of the chamber 230.

The small reactor 10 using a single 50 mW rated light emitting diode 100 with a 265 nm peak wavelength produces a dose of approximately 40 mJ/cm² at a 0.5 liters per minute flow in a spherical reactor 10 with a volume of only 0.3 cc (diameter of 0.8 cm) with the aperture 240 having an area 245 of 1 mm². This favorably produces a six-log reduction in the pathogen of interest (*E. coli*), or approximately a four-log reduction in the QBeta phage, which is widely used as a surrogate for estimating the effectiveness of UV irradiation against other pathogens.

Illustrative embodiments also may be used with fluid having a high absorption of UV light—i.e., fluids that run the risk of absorbing much of the UVC light before that light can impact the pathogens. For example, such fluids may include juices, plasma, visibly dirty or cloudy water, and/or water having high concentrations of pathogens. To that end, the size of the chamber 230 may be matched to the absorption length of the fluid being treated.

The maximum dose in a well-designed reactor 10 when used with such fluid may be simplified as follows when the size of the reactor is greater than or approximately equal to 1/α:

$$D = P_c/\alpha * f, \text{ where:} \qquad \text{Equation 3:}$$

Pc is the power from the light emitting diode 100 coupled into the reactor 10, α is the absorption coefficient of the fluid (and 1/α is the absorption length)

f is the liquid flow rate (volume per unit time).

The inventors recognized that an attractive feature of UVC light emitting diodes 100 is their very small footprints, which may allow small, low cost reactors 10 to be functionally feasible. However, prior art use of UVC light emitting diodes 100 in water disinfection reactors 10 known to the inventors use the sealed window 260 between the light emitting diode 100 and the fluid being disinfected.

This window 260 (typically quartz) is difficult to make as small as the light emitting diode 100. It is believed to be difficult to make a sealed quartz window smaller than 1 cm in diameter and, typically, it will be 2 cm in diameter or even larger. For a reactor 10 with a total volume greater than 100 cm³, for example, this window 260 size can still be a small fraction of the total surface area of the reactor 10. While the detailed geometry can change this value by a geometrical factor, for a spherically-shaped chamber 230 the internal surface area is proportional to the volume of the reactor 10 to the ⅔ power.

Thus, in this example, a 2 cm diameter window 260 takes up about 14 percent of the surface area of a 100 cm³ reactor 10 with a surface area of 22 cm². While a larger window 260 is generally favorable for capturing more of the light from the light emitting diode 100 (provides for a larger numerical aperture), for the water disinfection reactor 10, it is less efficient since the window 260 is not a reflecting surface. For instance, if a 100 cm³ water disinfection reactor 10 has the wall 220 that is 95 percent reflective, but the window 260 aperture 240 takes up 14 percent of the surface area, the average reflectivity of the reaction chamber will only be 0.86*0.95+0.14*0.0=0.82. This reduces the maximum dose (see Equation 1) by a factor of 3.6 compared to a reactor 10 where the aperture 240 for the light emitting diode 100 could be made much smaller (on the order of 0.01 cm²) as discussed above.

To reiterate, illustrative embodiments provide a number of advantages over the prior art. For example, illustrative embodiments enable making efficient small reactors 10 having a chamber 230 volume of less than 100 cc. Preferably, illustrative embodiments enable making the chamber 230 volume of less than about 10 cc. The reactor 10 is more efficient because it achieves a higher UVC dose for a given fluid flow for a single diode with a particular rated output power. To that end, illustrative embodiments couple more of the LED 100 output power into the reactor 10 through the small aperture 240 (e.g., having an aperture area 245 of less than 1.0 cm², and preferably less than 0.1 cm²).

Keeping the aperture 240 small with respect to the rest of the chamber 230 provides a number of advantages for small reactors 10, because illustrative embodiments rely on reflective walls 220 to achieve efficient fluent disinfection (e.g., by allowing the photons to have a long path length through multiple reflections off the walls 220). This effect is demonstrated in Equation 3. The RED that the reactor 10 can achieve is proportional to $(1-[R])^{-1}$ where [R] is the average reflectivity of the walls of the chamber. Even if the walls of the chamber 230 are made of a material with high reflectivity, the average reflectivity is reduced because the aperture 240 acts as an absorber. However, making the aperture 240 small in traditional ways reduces the amount of UVC radiation that is coupled into the chamber 230.

Figure 8:
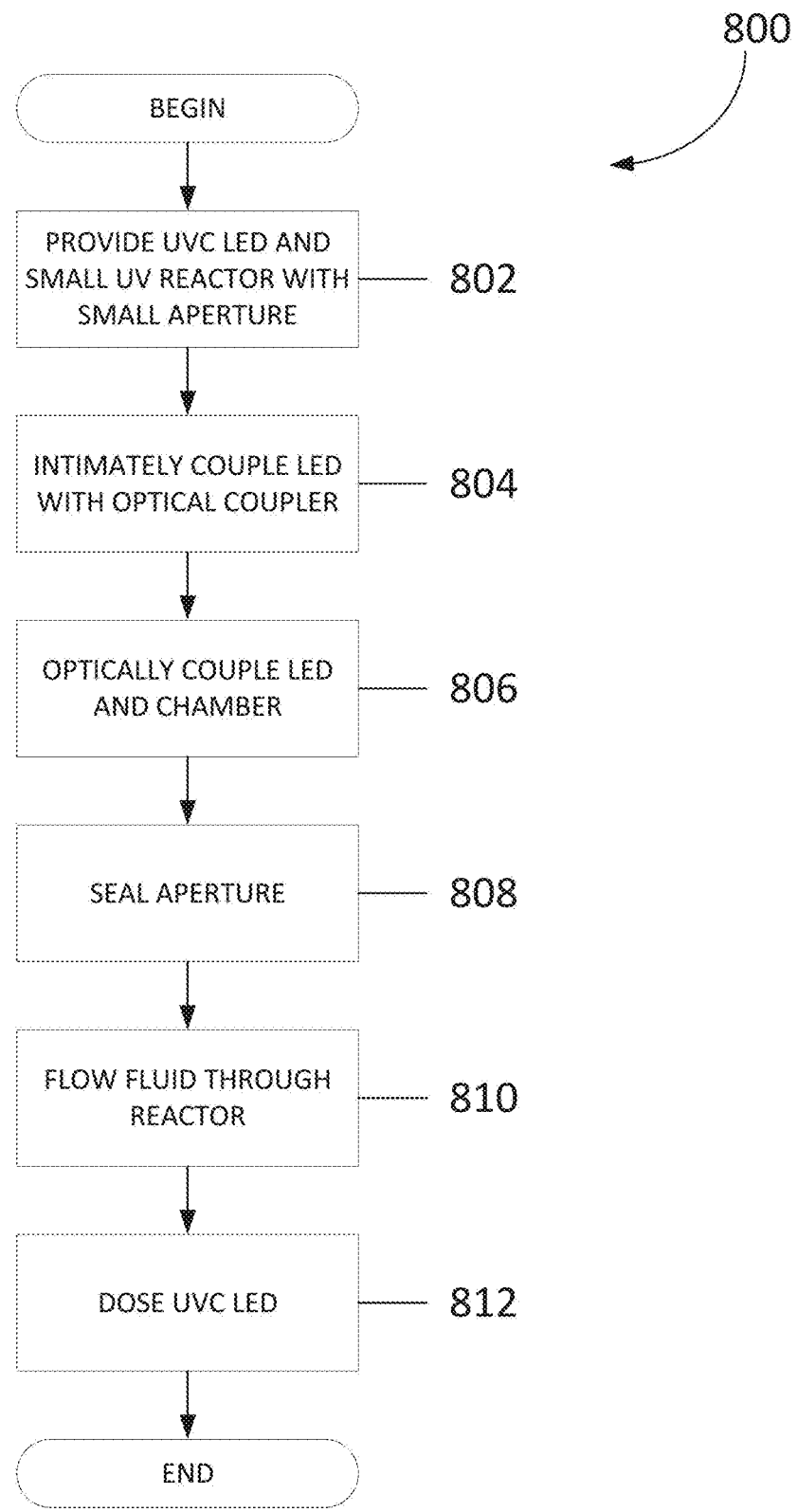
FIG. 8 shows a process of using the UV reactor in accordance with illustrative embodiments of the invention.

FIG. 8 shows a process 800 of using the UV reactor 10 in accordance with illustrative embodiments of the invention. The process begins at step 802, which provides the UVC LED 100 and the small UV reactor 10. As described previously, the UVC LED 100 may of the type having an exposed emission surface 150 and/or a covered radiation emission surface 150. As described herein, the exposed radiation emission surface 150 has certain advantages over LEDs having the lens/window 130 over the emission surface.

As described herein, the chamber 230 volume is less than 100 cc. In fact, illustrative embodiments facilitate production of so-called "mini-reactors 10" that are much smaller than 100 cm$^3$. Reactors 10 smaller than 50 cm$^3$ or even as small as 1 cm$^3$ (or even 0.5 cm$^3$) are desired for certain applications. It should be understood that reactor 10 size refers to the volume of the disinfection chamber 230. In this case, the average reflectivity of the chambers 230 of the reactor 10 is significant and the use of a relatively large input aperture 240 for the light emitting diode 100 undesirably can render the mini-reactor 10 untenable. For example, a 0.1 cm$^3$ reactor 10 may have a surface area of around 1 cm$^2$, which is the approximate size of even the smallest aperture 240 currently in use by the prior art. However, illustrative embodiments overcome that problem by permitting an aperture area of, for example, about 0.01 cm$^2$, which is only $^1$/$_{100}$ of the total reactor wall area. This favorably allows a high average reflectivity even when the light emitting diode input aperture 240 is averaged into the overall reactor area. In some embodiments, the small aperture 240 size is achieved only without the window 260 (which generally cannot be made smaller than 1 cm).

Illustrative embodiments enable a RED of at least 10 mJ/cm$^2$ for reactor 10 sizes ranging from about 0.004 cc to about 10 cc. More specifically, some embodiments enable a RED of greater than 16 mJ/cm$^2$ for similarly sized reactors 10. To that end, illustrative embodiments provide reactors 10 having an aperture surface area 245 that is between about 25.0% and about 0.001% of the total surface area of the chamber 230. In some embodiments, the reactor 10 size may range from about 5 cc to about 25 cc.

To provide a simplified example, assume the chamber 230 is a 0.1 cc cube-shape having dimensions 5 mm by 5 mm by 4 mm. The total internal surface area is 130 mm$^2$. A 1 mm$^2$ aperture is about 0.77% of the total surface area. As another example, the cube-shape chamber 230 volume of a 10 cc cube having dimensions 25 mm×20 mm×20 mm. The total internal surface area is 2800 mm$^2$. Therefore, a 1 mm$^2$ aperture is about 0.036% of the total surface area. Thus, in illustrative embodiments the aperture surface area may be between about 1.0000% and about 0.0001% of the total surface area.

While the above examples describe a substantially cube-shaped chamber 230, it should be understood that the shape of the chamber 230 may vary. For example, chamber 230 frequently have an elongated tube shape. The elongated tube shape is advantageous for making distance [r] long in a situation where the walls 220 are not reflective or have a much smaller reflectivity in other directions. Other chambers 230 may be spherically shaped to make the path length the same in all directions and to improve the uniformity of the irradiation in the reaction chamber 230. However, these conditions are not required for obtaining a reactor 10 with a high FOM, particularly when the volume of the reactor 10 is small.

Some embodiments may have a relatively narrow chamber 230 that is relatively narrow (e.g., ~1 cm diameter). A chamber 230 having dimensions of 1 cm×1 cm×100 cm has a volume of 100 cm$^3$. In this example, the chamber 230 has an internal surface area of 402 cm$^2$. If the aperture area 245 is 1 mm$^2$ (0.01 cm$^2$), the aperture 240 takes up about 0.0025% of the total surface area. If the aperture has dimensions of 0.5 mm×0.5 mm, it has a total aperture area 245 of 0.25 mm$^2$ (0.0025 cm$^2$). In such an example, the aperture area 245 is approximately 0.00062% of the total chamber 230 area. Even for a mini-reactor of about 100 cc volume, the small aperture 240 may not make an enormous difference to average reflectivity [R] because it is a small proportion of the total area.

Some embodiments may mitigate disadvantages of a large aperture 240 by maximizing the path length of the UVC light emitted by the UVC LEDs 100 before the light is reflected back toward the aperture 240, where the UVC radiation may escape or be absorbed. The fluid passing through the chamber 230 may be uniformly dosed by directing the UVC radiation along the same axis as the flow of the fluid (see, for example, the Klaran™ WR series UVC LED Reactor from Crystal IS or the Strike Platform from Acuva). This approach has the advantage of achieving a high FOM with a relatively large aperture 240 when compared to the UVC LED 100 size.

In some embodiments, shrinking the length of the chamber 230 rapidly decreases the FOM after the length of the chamber 230 gets smaller than the absorption length of the fluid (=1/α). For example, for fluid having an alpha of 0.105 cm$^{-1}$ (i.e., UVT of 90%), this length is about 10 cm. Illustrative embodiments may provide LED 100 radiation emitted along the flow line (e.g., along the longitudinal axis of the reactor 10). To that end, LEDs 100 may be positioned along the endwalls of the reactor 10 rather than the sidewall 220. However, to accommodate the LEDs 100 in the endwall, the inlet 232 and/or the outlet 234 may have to be repositioned such that they are non-parallel with the longitudinal axis of the reactor 10. This arrangement may, in some embodiments, undesirably add cost to the system.

Accordingly, illustrative embodiments provide an efficient in-line fluid disinfection system with UVC LEDs 100 that radiate into the reactor chamber 230 from the sidewall 220 (e.g., as shown in FIG. 4) instead of, or in addition to, the endwalls. The orientation of the LEDs 100 on the sidewall causes the effective path length [r] of the UVC light before it hits the wall 220 of the chamber 230 to be approximately the diameter of the chamber 230 (as shown in FIGS. 4 and 5). The reactor 10 thus may have a good FOM (if the average reflectivity [R] is high), because the UVC light reflects multiple times before being absorbed or escaping the chamber 230. In addition, multiple reflections help achieve a more uniform fluence of the fluid passing through the chamber 230. The uniformity of fluence is improved as the diameter of the chamber 230 decreases to less than 0.7 of the absorption length (=1/α) when the average reflectivity [R] is greater than approximately 85%. Illustrative embodiments achieve average reflectivity [R] of greater than 85% for small diameter chambers 230 by making the aperture(s) 240 small.

In illustrative embodiments, the in-line fluid disinfection reactor 10 has LEDs 100 oriented to emit light in a direction that is substantially perpendicular to the flow path (e.g., transverse to a longitudinal axis of the chamber 230), as shown in FIGS. 4 and 5. Accordingly, illustrative embodiments may have one or more LEDs on a sidewall 220 of the chamber 230. The in-line reactor 10 makes it easier to design a longer chamber 230 with more LEDs 100 coming in from the side (perpendicular to the water flow) as shown in FIG. 4. Additionally, or alternatively, it may be advantageous to gang together two or more in-line reactors to achieve equivalent UVC doses.

In some embodiments with in-line flow where a large proportion of the UVC radiation is not absorbed by the walls 220 of the chamber 230, it may be advantageous to make the length of the reactor 10 longer than twice the absorption length (2*(1/α)). Preferably, the aperture 240 is located in the middle of the length of the chamber 230. For example, for a fluid having 90% UVT or greater, a is about 0.105 cm$^{-1}$ or less. Accordingly, in some embodiments, it is advantageous to make the length of the reactor 10 at least about 19 cm or greater. This length assists with obtaining high efficiency and reducing the amount of radiation from escaping out of the inlet 232 or the outlet 234. Alternatively, the inlet 232 and outlet 234 may be tapered (as shown in FIG. 4) and/or shielded in such a way as to reflect the UVC radiation back into the reaction chamber 230.

For a small reactor 10 having a 10 cc chamber 230, the size of the aperture 240 is also considerably more important than in a large reactor 10. A 10 cc elongated chamber 230 having dimensions of 1 cm×1 cm×10 cm has a 42 cm$^2$ internal surface area. Assuming the aperture area 245 has dimensions of 1 mm$^2$, the aperture 240 takes up 0.023% of the total surface area of the chamber 230.

For a small reactor 10 having a 1 cc chamber 230, the size of the aperture becomes even more important. A 1 cc cubical chamber (e.g., 1 cm×1 cm×1 cm) has a 6 cm$^2$ surface area. For a 1 mm$^2$ aperture area, the aperture takes up 0.17% of the total surface area.

For an even smaller reactor 10, such as one having dimensions of 0.5 cm×0.5 cm×0.5 cm (volume of 0.125 cm$^3$), the total internal surface area of the chamber 230 is 1.5 cm$^2$. Illustrative embodiments having a 5 mm×5 mm aperture 240 have about up to 17% of the total surface area of the chamber 240 taken up by the aperture 240.

As can be seen from FIG. 8, the smaller the α[r], which is a function of the size of the reactor 10, the less the FOM. Indeed, for small reactors 10 having an alpha*[r] of 0.001, a reduction in average reflectivity [R] of only 2% drops the FOM from 1.00 to less than 0.1. For a slightly larger reactor 10 having an a [r] of 0.02, the same 2% change in reflectivity [R] drops the FOM to about 0.5. In contrast, for a reactor having an alpha*[r] of 5, a 2% drop in reflectivity [R] has negligible effect on the FOM value.

Because illustrative embodiments operate with small reactors (where [r] is small), and alpha (α) is a property of the fluid, it is advantageous for the average reflectivity [R] to remain high within the chamber, in order to keep the FOM high (and ensure that the fluid and particles therein absorb the UV light). For that reason, illustrative embodiments maintain a small aperture area 245 in order to keep average reflectivity [R] high. Additionally, illustrative embodiments use the optical coupler 250 to increase the amount light that makes it into the chamber 230.

Returning to FIG. 8, the process then moves to step 804, which intimately couples the LED with the optical coupler 250. As described previously, the optical coupler 250 increases the total amount of UVC radiation extracted from the chip 110 (see FIGS. 9A-9B for example). The optical coupler 250 may be provided in a first substantially non-solid phase. In some embodiments, the optical coupler 250 may be a gooey consistency, into which the chip 110 may be pressed directly. The intimate contact allows the optical coupler 250 to come very close to the LED (e.g., within a distance that is less than a quarter wavelength of the emitted UVC light). Thus, preferably, intimate contact is established by allowing the optical coupler 250 to come within at most 70 nm distance from the emission surface 150.

In various embodiments of the invention, the optical coupler 250 may be silicone-based, and may be formed from, for example, Deep UV-200 available from Schott North America, Inc. of Elmsford, N.Y., or a similar material.

The process then moves to step 806, which optically couples the LED and the chamber 230. This may include placing the LED directly against the window 260. In some other embodiments, the LED may be coupled with a light pipe that couples light into the chamber 230.

Preferably, illustrative embodiments optically couple by positioning the optically coupler 250 between the LED 100 and the chamber 230. As shown in FIGS. 6B-6E, there are a number of ways the optical coupler 250 can be positioned between the chamber 230 and the LED 100. This includes embodiments in which the optical coupler 250 does not enter the aperture 240. This also includes embodiments in which the optical coupler 250 enters the aperture 240 and/or the chamber 230.

The process then proceeds to step 808, which seals the aperture 240. The aperture 240 may be sealed using the sealing member 260 (such as a quartz window). However, in preferred embodiments, the aperture 240 is sealed by the optical coupler 250 (e.g., see FIG. 6B). In some embodiments, the sealing is accomplished by positioning the optical coupler 250 between the LED 100 and the chamber 230, and therefore, the steps are the same. In some other embodiments, the chamber 230 may be sealed by curing the optical coupler 250. By curing the optical coupler 250, the optical coupler may transition to a second substantially solid phase. Accordingly, a fluid tight seal is formed with the aperture 240, and fluid does not escape the chamber 230. This provides the advantage of reducing the number of interfaces between the emission surface 150 and the fluid in the chamber 230. Additionally, the optical coupler 250 contacting the fluid directly provides for heat management (e.g., without soldering the LED to a heat sink, and thereby maintaining intimate coupling that may otherwise be destroyed because of thermal expansion indices mismatches).

The process then proceeds to step 810, which flows the fluid. As described previously, the fluid may be drinking water. To that end, the flow may flow through a straw embodiment (e.g., when a user is drinking from the straw). Alternatively, the fluid may flow through a sink and/or a water dispenser.

As the fluid flows through the reactor 10, it may cool heat generated by the LED 100, which is conducted into the chamber 230 by the optical coupler 250. Thus, illustrative embodiments advantageously avoid having a bulky heat sink 210 or a complicated heat pipe (thermal connection to some other heat sink such as the fluid itself). Instead, illustrative embodiments may use the front (emission) surface 150 of the LED 100. This may be accomplished by keeping the light extraction membrane (e.g., optical coupler 250) very thin (and thus reducing the thermal resistance) and directly coupling to the LED semiconductor chip surface 150 or by making a direct thermal connection to the surface of a high thermal conductivity LED package 120 (such as what is used for Klaran™ UVC LEDs). Klaran™ diodes 110 are also attractive for this application because they are fabricated on AN substrates, so the emission surface 150 has high thermal conductivity compared to UVC LEDs 100 that are based on sapphire (which has a factor 10 lower thermal conductivity). Furthermore, the inventors believe that sapphire based LEDs 100 are more sensitive to moisture, and therefore, may require the lid 130 and are not as reliable when intimately contacting some embodiments including the optical coupler 250. Accordingly, the optical coupler 250 may also act a thermal coupler.

As the fluid flows, the process may proceed to step 812, which doses the UVC LED 100. The UVC LED 100 may be dosed to achieve a minimum RED, such as at least 10 mJ/cm². Additionally, the UVC LED 100 may be dosed in accordance with a variety of triggers, described herein and in the applications incorporated by reference. The process then comes to an end.

It should be noted that the process 800 is a simplified version of a more complex process of using the reactor 10. As such, the actual process may have additional steps that are not discussed. In addition, some steps may be performed in a different order, or in parallel with each other. For example, steps 810 and 812 may be performed simultaneously, and continuously. Indeed, step 810 may trigger step 812. In some embodiments, some steps may be duplicative and/or removed altogether. For example, sealing the aperture and optically coupling the LED and the chamber may be the same step in some embodiments. Accordingly, discussion of this process is illustrative and not intended to limit various embodiments of the invention.

FIGS. 9A-9D show examples of increased UVC dosage available in the chamber 230 in accordance with illustrative embodiments of the invention. FIGS. 9A-9D show an example where a single UVC diode 100 is used in the water disinfection reactor 10. The diode 110 is assumed to emit radiation UVC radiation with a peak wavelength in the range of 260 to 270 nm. The diode 110 has a bare semiconductor surface, such as provided by commercially available Klaran diodes 110B. The diode 110 may be selected from a power bin which ranges from 60 mW to 70 mW. To be specific, for the purpose of illustration, the diode 110 is assumed to have a power of 62.5 mW. Additionally, the fluid is assumed to have an alpha (α) of 0.105 cm⁻¹ (i.e., UVT of 90%).

Figure 9A:
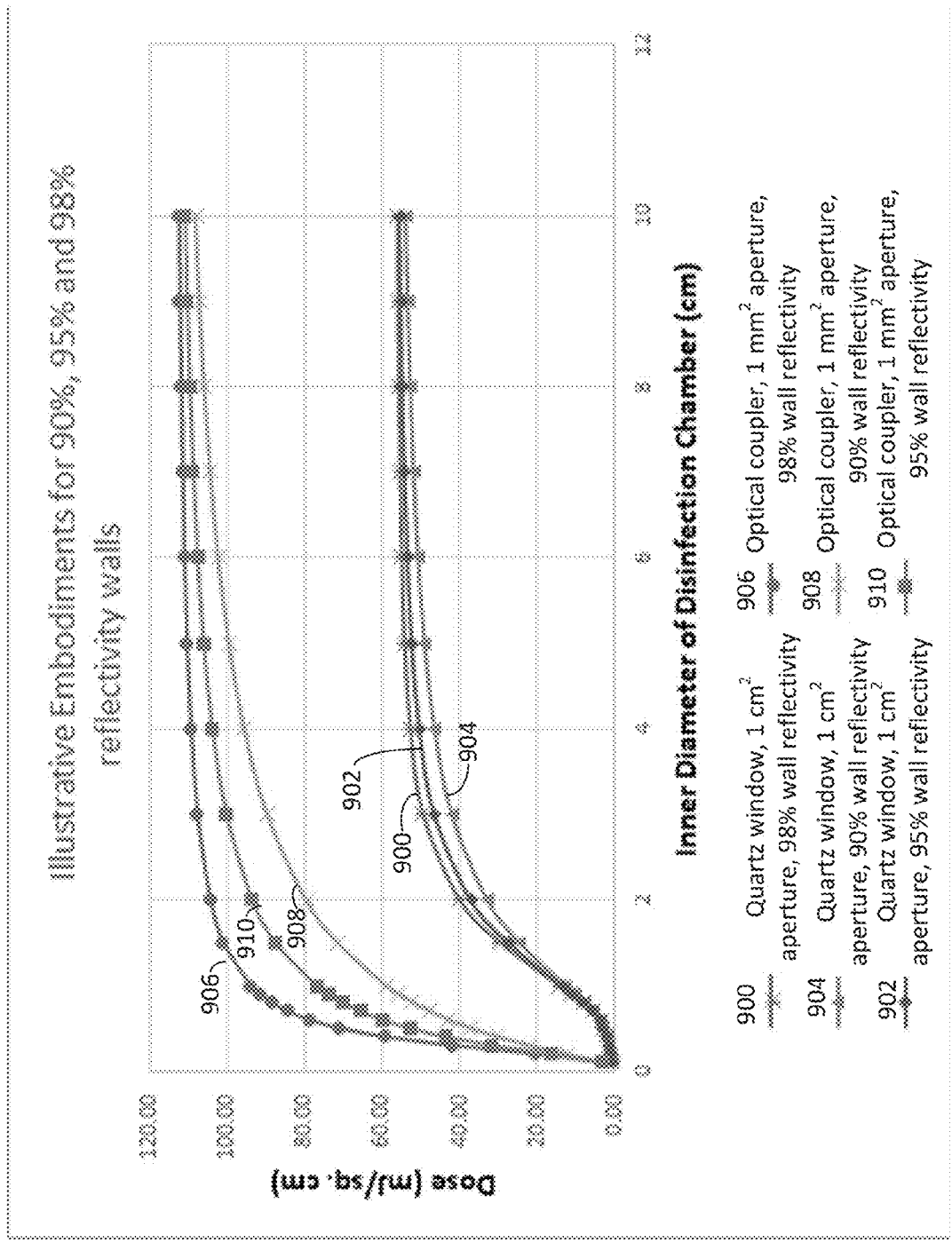
FIGS. 9A-9D show examples of increased UVC dosage available in the chamber in accordance with illustrative embodiments of the invention.

FIG. 9A shows a chart of UVC reduction equivalent dose in the chamber 230 for various disinfection chamber 230 diameters. The chart shows plots 900-904 of LEDs 100 having a chip 110-air interface (e.g., a quartz window with no intimate coupling), and a 1 cm² aperture 240. The chart also shows plots 906-910 of LEDs 100 having a chip 110-optical coupler 250 interface, and a 1 mm² aperture 240 in accordance with illustrative embodiments. Additionally, three different wall 220 reflectivities (90%, 95%, and 98%) are shown for each of the above described configurations. The reflectivities are the reflectivity of the wall 220, not the average reflectivity [R], which would include the area 245 of the aperture 240.

For example, when the diameter of the spherical chamber 230 is 10 cm, the volume in the chamber 230 is about 520 cc. As an additional example, when the diameter is 4 cm, the volume in the chamber 230 is about 34 cc. Thus, illustrative embodiments may have the chamber 230 volume of about 35 cc or less.

FIG. 9A shows that the optical coupler 250 (e.g., plots 906-910) provides approximately a 2× increase in RED in the chamber 230 at larger volumes. This effect is clear at larger volumes, becomes the effect of the smaller aperture size becomes negligible. The inventors have determined in experiments done with optical couplers 250 formed from silicone that the dosage may be increased to above 2× by configuring the optical coupler 250 in such a way as to create a more convex surface at the fluid interface inside the reactor 10. Additionally, using a silicone (or other UV transparent moldable material that allows intimate contact with the LED chip surface 150) with a higher index of refraction by, for instance, doping so that the optical coupler 250 has an index closer to the emission surface (which is AlN for the Klaran™ diode with an index of 2.5). Furthermore, making a hemispherical surface at the water interface, could dramatically improve the optical coupling. Further improvement is also possible by making the walls of the optical coupler 250 reflective. The inventors recognized that improvements in optical couplers 250 could increase the photon extraction by a total of 5× (output 500% of the rated power of the LED 100). For example, because of the high index of refraction of AlN of the commercially available Klaran™ diode, a total of 5× improvement in the UVC light delivered to the fluid disinfection chamber 230 can be achieved over the rated LED 100 power. Thus, some embodiments may output about 500% of the rated power of the LED 100, or at least 400%, 300%, or 250% of the rated power of the LED 100.

Figure 9B:
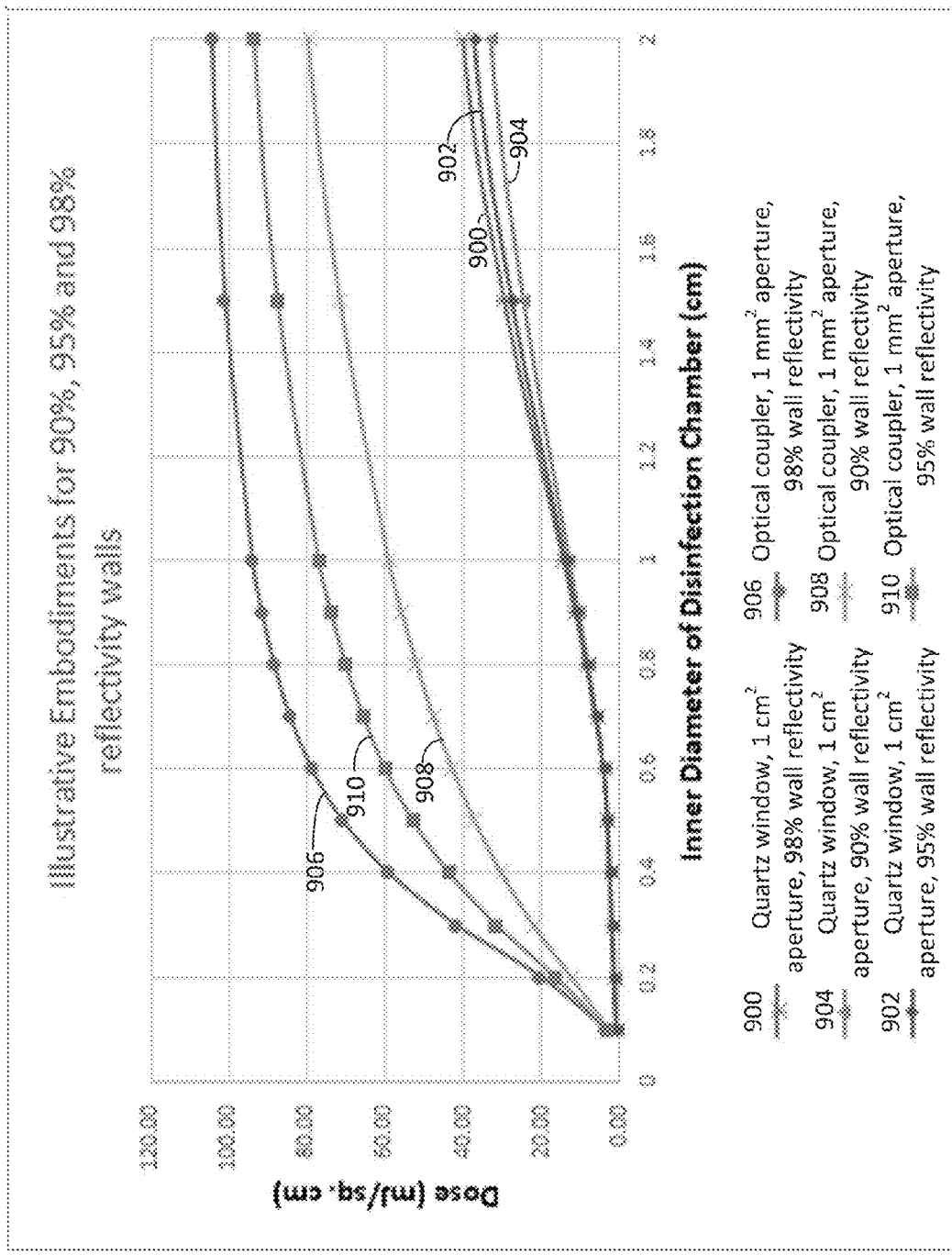

FIG. 9B schematically shows a close-up of FIG. 9A for small diameter chambers 230. As can be seen from the chart, when the diameter of the spherical chamber 230 is between 0.2 cm and 0.5 cm, illustrative embodiments having the optical coupler 250 and the smaller aperture 240 (e.g., plots 906-910) may have an LED dosage of between at least about 5-10 times greater than illustrative embodiments with a quartz window (no optical coupler) and a larger aperture 240 (e.g., plots 900-904). Similarly, for slightly larger diameters of between about 1 cm and about 2 cm, illustrative embodiments having the optical coupler 250 and the smaller aperture 240 may have an LED dosage of between at least about 2.5-5 times greater than illustrative embodiments with no optical coupler and the larger aperture 240.

For an aperture area 245 of 1 cm², at most about 80% of the output radiation is coupled into the chamber 230. Thus, for the 62.5 mW output, the power into the chamber 230 $P_C$ is 50 mW. Illustrative embodiments having an aperture area 245 of 1 mm², and using the optical coupler 250, couple at least 160% of the radiation into the chamber 230. Thus, for the 62.5 mW output, the power into the chamber 230 $P_C$ is 100 mW.

The reason for the higher power coupling, as has been explained previously, is due to the increased photon extraction that is possible from the semiconductor surface 150, which has a high index of refraction. The optical coupler 250 is especially advantageous when the surface 150 of the LED diode 110 is the high index material used for the emission of the UVC radiation (e.g., for Klaran diodes 110B, that surface will be AN with an index of refraction of about 2.5 while for other types of commercial diodes 110A, it may be a sapphire surface with an index of refraction of about 1.8 in the UVC range). For the purposes of illustration, assume that the reactor chamber 230 is configured to disinfect drinking water with a UVT that is 90% or greater (for the example, 90% is used). Again for discussion purposes, the reactor 10 is assumed to be designed as a sphere so that the average optical path [r] is exactly the diameter of the sphere and the surface area of the sphere is π[r]² (where [r] is the diameter of the sphere, not the radius).

For small reactors 10, efficiency is greatly enhanced when the inner surface 225 is reflective to increase the effective path length [r] of the emitted photons rather than letting them be absorbed by the walls 220 of the reactor chamber 230. The average reflectivity of the chamber [R] is calculated to be [R]=R×(1−(total area of the apertures)/(total area of inner chamber surface)) where R is the reflectivity of the chamber wall 220. For this example, R is assumed to be constant everywhere except for where the aperture 240 is located. FIG. 9A shows the results of calculations of the total RED that is possible for chamber walls with 90%, 95% and 98% reflectivity such as could be provided by aluminum or PTFE surfaces when the water flow is 0.5 liters/min. Even for relatively large chambers 230 (where [r] is 10 cm or greater), illustrative embodiments provide substantial advantage because of the improved coupling of UVC radiation into the reactor chamber 230 (approximately double what is possible using quartz windows 260). However, the advantage become enormous for mini reactors 10. Accordingly, illustrative embodiments enable small reactors 10 that efficiently disinfect fluid flowing therethrough.

The UVC dose required depends on the application. However, the NSF uses 40 mJ/cm$^2$ for class A reactors (this is defined at 254 nm, the dose required at 265 nm is approximately 15% lower) and 16 mJ/cm$^2$ for class B reactors. Class A reactors are desirable where greater safety is needed. Smaller reactors could be raised above these limits by using either higher power diodes 110 (the dose is approximately proportional to the rated power of the diode 110) or by reducing the water flow (the dose is approximately proportional to the inverse of the water flow).

In some embodiments, the light emitting diode 100 input aperture 240 is small and may be configured to be extremely effective in coupling the photons generated in the semiconductor with the fluid to be disinfected. The standard arrangement of going from semiconductor to air to quartz to water results in more than a factor of 2.0 loss of radiation compared to illustrative embodiments. This is because the index of refraction of the semiconductor can be high (e.g., about 2.5) while that of water is 1.3 and that of air is 1.0. The combination of these effects can make reactors 10 smaller than 100 cm$^3$ significantly more efficient, and importantly, make reactors 10 as small as 1 cm$^3$ or smaller functionally feasible for disinfecting fluids.

Figure 9C:
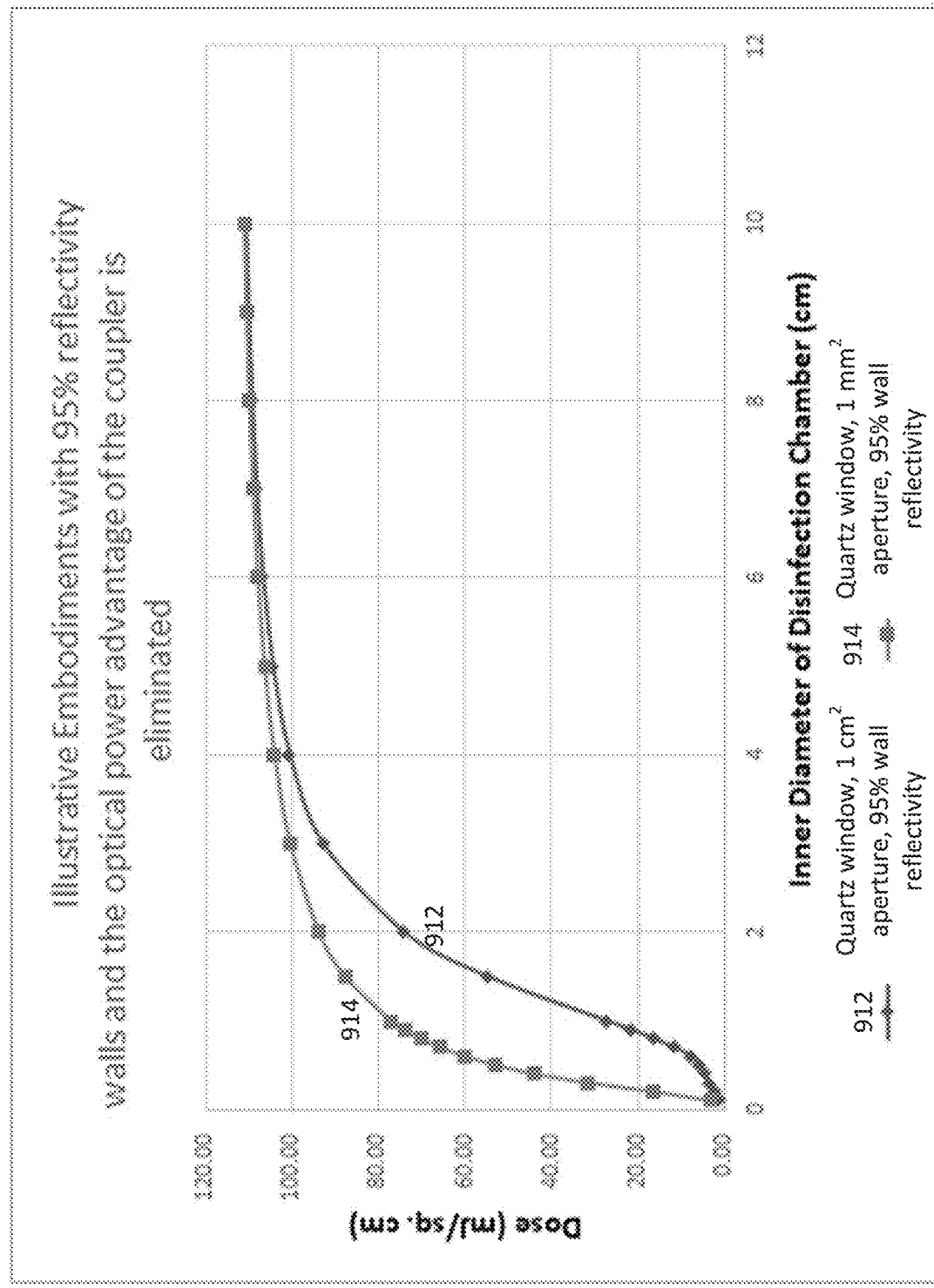
Figure 9D:
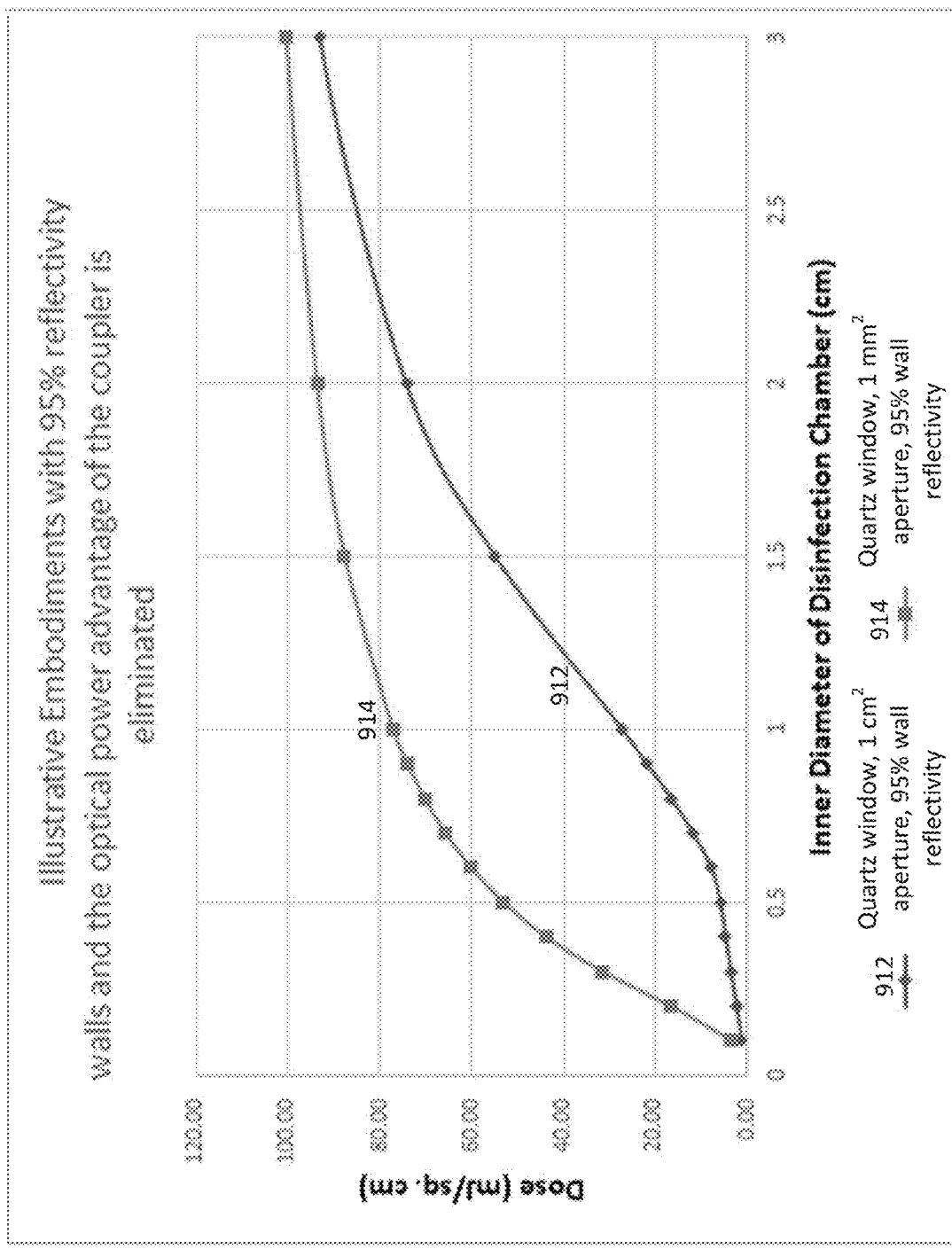

FIGS. 9C-9D show configurations of LEDs 100 where the power coming into the two chambers 230 were equal (e.g., no optical coupler 250 in both), but the aperture 240 sizes are different. Plot 912 shows a 1 cm$^2$ aperture 240, while plot 914 shows a 1 mm$^2$ aperture 240. FIGS. 9C-9D consider the situation where $P_C$ is kept at 100 mW for the reactors 10. This could be done, for instance, by finding a UVC diode capable of producing 125 mW. As FIGS. 9C-9D show (FIG. 9D has the x-axis expanded), the advantage of the small aperture 240 becomes significant as the chamber 230 diameter shrinks below 3 cm, which corresponds to the chamber 230 volume of about 14 cc or smaller. Accordingly, at small chamber volumes (e.g., 20 cc or less) the small aperture 240 of illustrative embodiments provides a considerable advantage in UV RED.

Illustrative embodiments also provide advantages in cooling the LED 100. For example, the standard heat sinking of the light emitting diode 100 through the back side of the light emitting diode 100 (the non-emission surface) typically requires a good thermal connection to the heat sink 210. This often requires the light emitting diode 100 to be soldered to a material with sufficient thermal conductivity to allow the heat to be transported to the heat sink 210. Typically, this is accomplished using a metal-core, printed circuit board (PCB). In contrast, illustrative embodiments cool the LED 100 from the top surface (also referred to as the front of the LED 100) by transporting heating directly into the fluid being irradiated. This not only eliminates the cost of the heat sinking arrangement but makes the insertion of the light emitting diode 100 much less costly since spring contacts 6F can be used to make the electrical connections to the light emitting diode 100 without necessitating soldering to a PCB. The inventors discovered that the high temperatures caused by soldering may destroy the intimate contact established with the optical coupler 250 because of thermal expansion mismatches of the optical coupler 250 and the semiconductor (e.g., chip 110). Therefore, by cooling the LED from the front, instead of requiring soldering the LED 100, allows the optical coupler 250 to stay in intimate contact with the LED 100 (e.g., with the chip 110).

Illustrative embodiments therefore solve multiple problems with small disinfection reactors 10 by improving uniform treatment with a minimal light aperture 240, and improving thermal management by using the fluid being treated as a coolant.

Figure 10A:
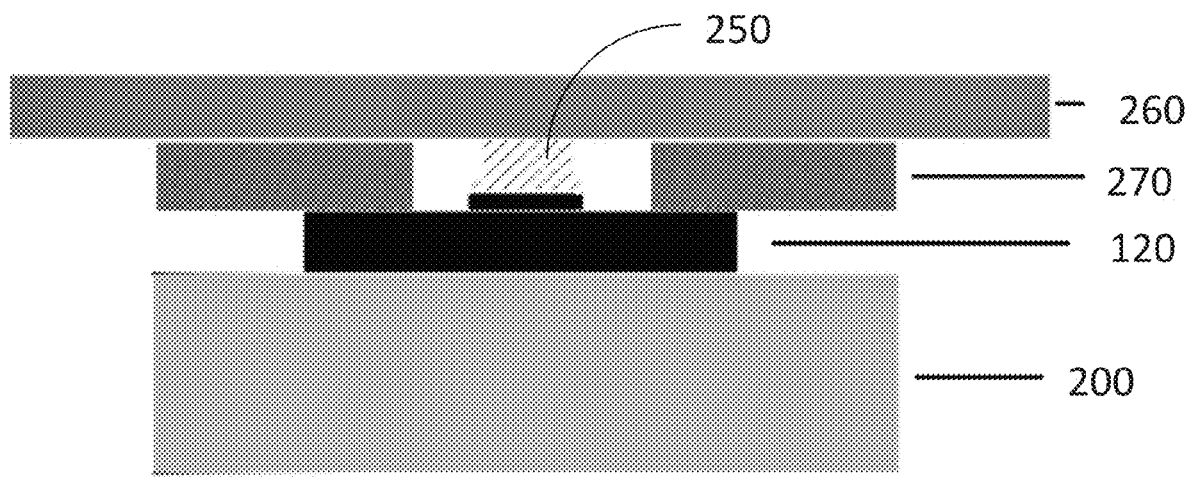
FIG. 10A schematically shows a configuration for thermal management of the LED in accordance with illustrative embodiments of the invention.
Figure 10B:
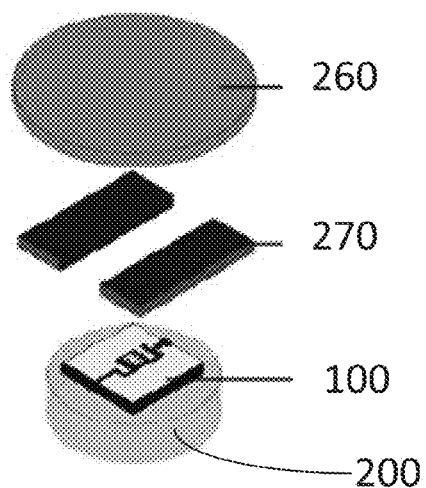
FIG. 10B schematically shows a perspective view of the heat transfer material in accordance with illustrative embodiments of the invention.

FIG. 10A schematically shows a configuration for thermal management of the LED 100 in accordance with illustrative embodiments of the invention. As shown, the LED 100 may optionally have the optical coupler 250, which may also transfer heat. To further increase heat transfer, illustrative embodiments may include heat transfer material 270, such as copper or alumina strips. The heat transfer material may have a 0.50 mm thickness. A small amount of non-conductive thermal transfer adhesive tape may be used at the top and bottom of the material 270 to couple the material to the window 260 and the package 120, respectively. In illustrative embodiments, the window 260 may be formed from sapphire, which has a high thermal conductivity. Accordingly, the sapphire window 260 may act as a heat spreader for better conducting heat into the chamber 230. In illustrative embodiments, the sapphire window 260 may have about an 8.5 mm diameter and a 0.50 mm thickness/height. The heat transfer material may be in the shape of a washer. FIG. 10B schematically shows a perspective view of the heat transfer material 270 in the shape of two bars in accordance with illustrative embodiments of the invention.

Figure 10C:
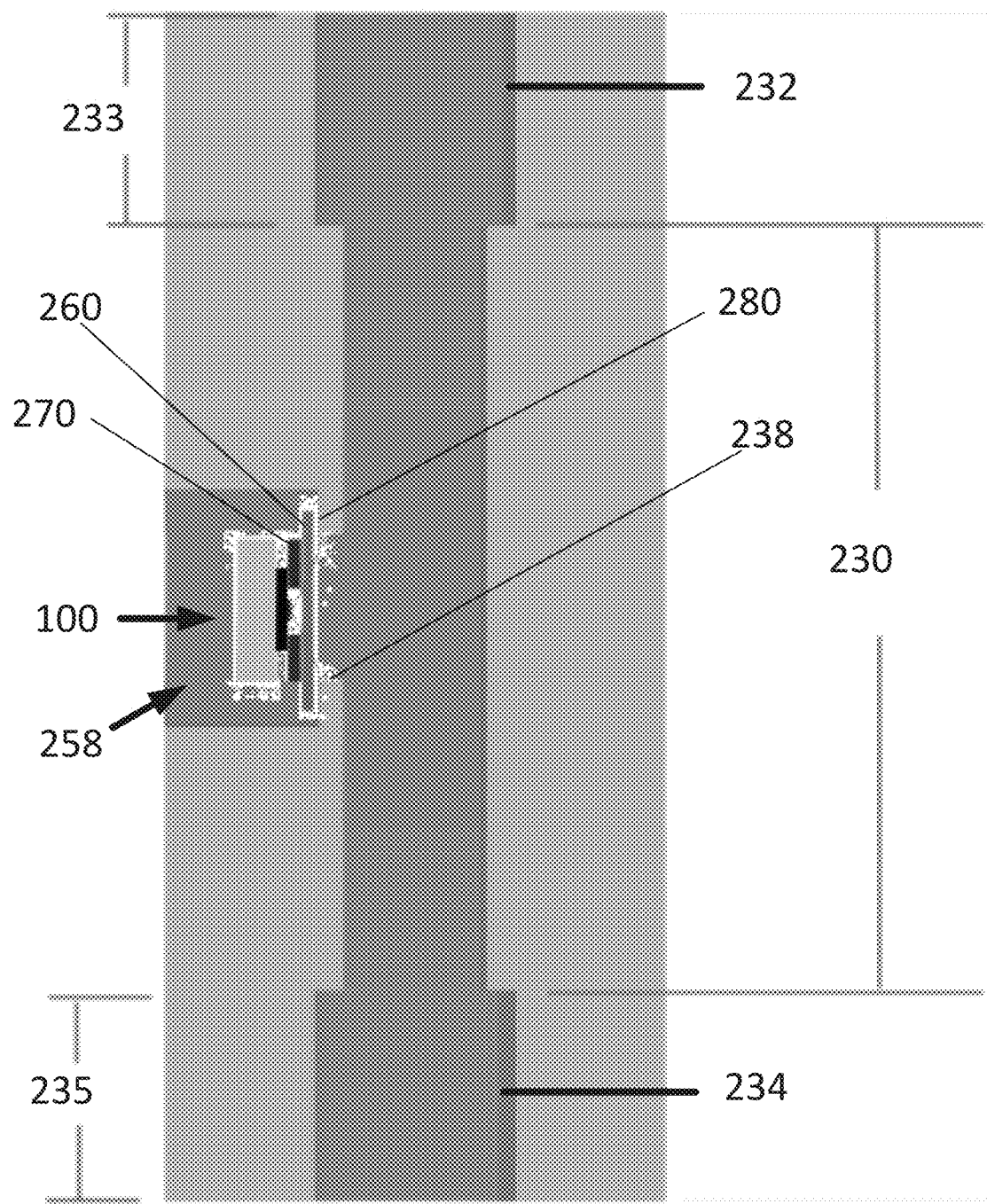
FIG. 10C schematically shows a sectional view of the LED of FIG. 10A positioned against the chamber.

FIG. 10C schematically shows a sectional view of the LED 100 of FIG. 10A positioned against the chamber 230. The chamber 230 may be, for example, a 6 mm diameter hole having a length of about 30 mm. The chamber 230 may be bored from a 20 mm×20 mm PTFE cylinder. In a similar manner, a threaded hole may be bored for an inlet 232 connector and/or an outlet 234 connector. In illustrative embodiments, the threaded holes 233 and 235 may each be about 9 mm to 10 mm long with a diameter of about 8.8 mm. The sapphire window 260 may be placed up against the aperture 240 of the chamber 230. The aperture 240 may have, for example, a 6 mm diameter. In some embodiments, the chamber 230 may have a reflective shoulder 238, which may be about 1 mm to about 2 mm deep. An LED receiving portion 258 may be a 10 mm diameter access hole that is about 5 mm to about 6 mm deep. The sapphire window 260 (which may be approximately 8.6 mm in diameter) may rest up against the shoulder 238 and the opening of the chamber 230. Accordingly, the increased surface area of the sapphire window 260 against the thermally conductive shoulder 238 and/or the opening of the chamber 230 may increase heat flux, thereby better cooling the LED 100.

Figure 11A:
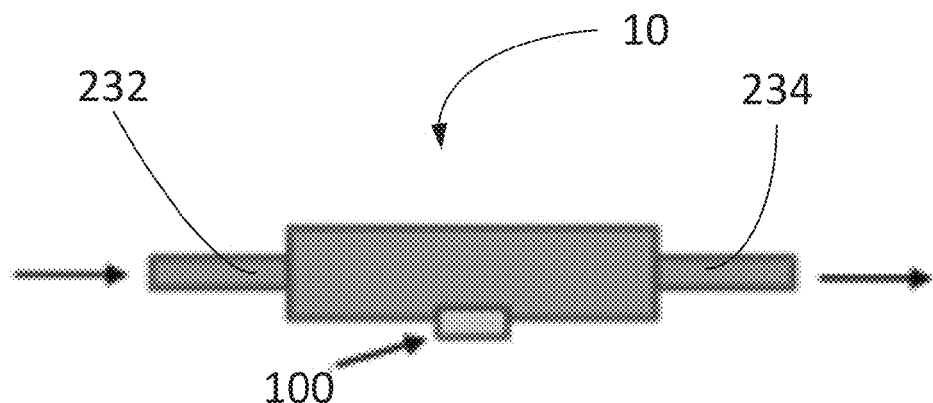
FIGS. 11A-11E schematically show various arrangements of reactors in accordance with illustrative embodiments of the invention.

FIGS. 11A-11E schematically show various arrangements of reactors 10 in accordance with illustrative embodiments of the invention. Specifically, FIG. 11A shows a single reactor 10 having the fluid flow inlet 232 and the fluid flow outlet 234. In FIGS. 11A-11D, fluid flow is represented by arrows entering the inlet 232 and exiting the outlet 234. As described previously, the reactor 10 may have one or more LEDs 100. However, a single LED 100 is shown for convenience, with the understanding that such arrangement and quantity is not limiting to various embodiments of the invention.

Figure 11B:
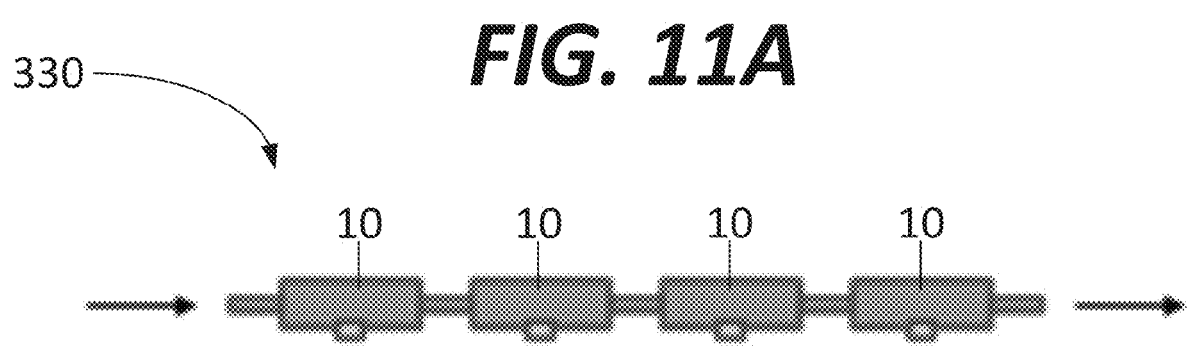

FIG. 11B schematically shows an in-series arrangement 330 of the reactors 10. The in-series arrangement 330 advantageously provides improved disinfection over a single reactor 10. Specifically, the fluid is treated by a first reactor 10, exits the outlet 243 of the first reactor 10, and enters the inlet 232 of a second reactor 10. This flow path may be repeated for as many reactors 10 as are in the series. Each of the reactors 10 individually may each provide an identical (or different) log reduction of pathogens at a particular flowrate. For instance, each reactor 10 may provide a 3-log reduction of pathogens at a flow rate of 0.5 L/min.

The inventors believe that the in-series arrangement 330 can reliably achieve an additive log-reduction per additional reactor in series when all else is constant (e.g., the four reactors 10 of arrangement 330 may provide a 12-log reduction of pathogens at a flow rate of 0.5 L/min, assuming that each of the reactors provides a 3-log reduction of pathogens at a flow rate of 0.5 L/min). As a further example, if a single reactor provides a 4-log reduction, two reactors in-series provide an 8-log reduction, three reactors in-series provide a 12-log reduction, etc.

Illustrative embodiments advantageously enable small-chamber reactors having a relatively small chamber 230 surface area. For reactors having UV-C highly reflective walls (e.g., formed from PTFE), the cost of materials can be significant. For example, the cost may scale with the square of the linear dimensions of the reactor chamber (i.e., if the size of the chamber is cut by ½, the amount of the reflective material that covers the inside of the chamber is cut by ¼). By providing the smaller chamber 230 reactors (e.g., 1 cm long by 0.5 cm diameter) in accordance with illustrative embodiments, the reactors 10 can be economically made with UVC reflective materials. A large majority of expense for a larger reactor 10 is proportional to the area of the wall 220 formed from and/or coated with the UVC reflective material. The size of various embodiments may range from, for example, 5 mm in length and 5 mm in diameter to 10 cm in length and 5 cm in diameter. Illustrative embodiments thus advantageously enable economic scale for multiple reactors 10 in-series and/or in-parallel. This is in contrast to expensive prior art reactors with large chambers surface areas having lengths between 10 cm and 30 cm, and diameters between 3 cm and 15 cm.

Assuming that the fluid that travels from one reactor 10 to the next reactor 10 is thoroughly mixed, the log reduction of the in-series arrangement 330 may be assumed to be the sum of the reduction of each of the individual reactors 10. A large log reduction is difficult to prove in practice because large log reduction requires an initial high concentration of the pathogen being tested in order to have a statistically relevant number of pathogen remaining after treatment. This high concentration may be hard to quantify and tends to increase the opacity of the fluid being treated. Accordingly, the improved log reduction of the in-series arrangement 330 is easier to qualify because the log reduction of an individual reactor is much smaller and does not require such a high initial concentration.

Figure 11C:
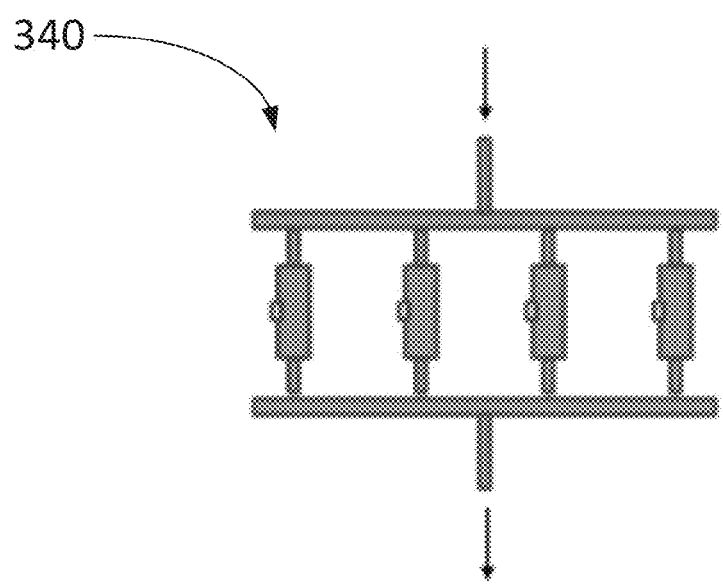

FIG. 11C schematically shows a parallel arrangement 340 of the reactors 10. Assuming that the reactors 10 used in the parallel arrangement 340 are substantially the same as the reactors 10 uses in the in-series arrangement 330, the parallel arrangement 340 provides increased maximum flow rate. However, combining the reactors 10 in parallel does not obtain the log reduction advantage of the in-series arrangement 330 when the log-reduction of the individual reactors 10 is maintained the same. As an example, if a single reactor 10 passes a flow rate of 4 L/min with 3-log reduction, the arrangement of four reactors 10 in parallel can pass a flow rate of 16 L/min with the same 3-log reduction. Thus, in this example, the four reactors in parallel are able to provide the same log reduction as a single reactor but at 4 times the flow of a single reactor.

Figure 11D:
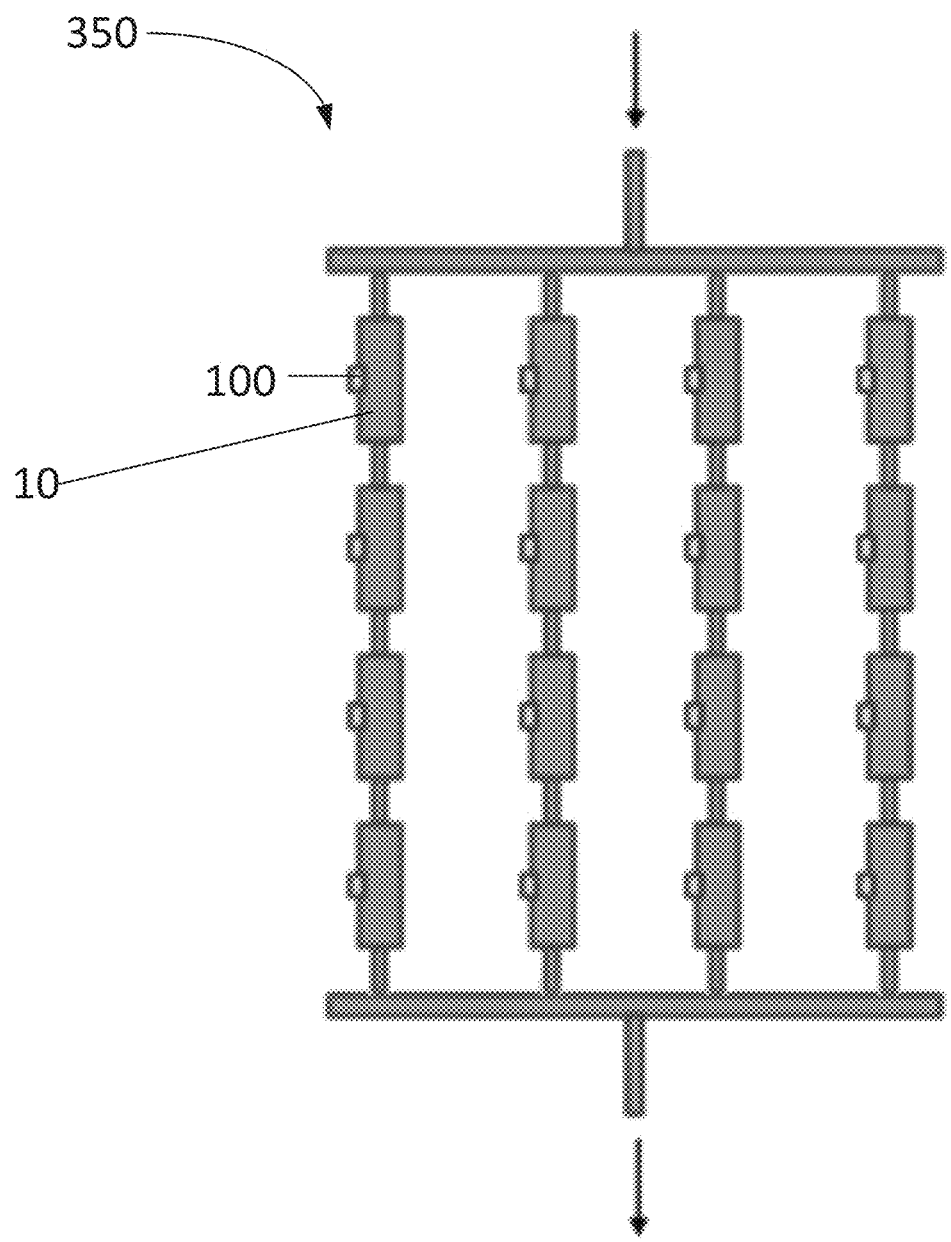

FIG. 11D shows a combined arrangement 350 including in-parallel and in-series reactors 10. The combined arrangement 350 advantageously benefits from both the increased log reduction of pathogens within the fluid that passes through the reactor 10, as well as increased fluid flow rates. In the example shown, if each of the small reactors 10 are rated at 2 log reduction at a flow of 1 L/min, then combination shown of 16 of these reactors will be capable of 8 log reduction at a flow of 4 L/min. Furthermore, a variety of numbers of reactors 10 may be used. Accordingly, illustrative embodiments are not limited to the number of reactors 10 shown in each series, nor are they limited to the numbers of in-series arrangements shown. However, it should be understood that the advantages described above regarding the in-series additive log-reduction increase and the in-parallel additive fluid-flow increase may be used in various combinations to achieve desired log-reduction and fluid-flow outcomes.

For example, some of the in-series reactors of the combined arrangement 350 may have varying numbers of reactors, as opposed to the same number in each series shown in FIG. 11D. Each of the reactors 10 may also include a variety of different types of LEDs 100 (such as the type of LEDs 100A and 100B described previously). Each reactor 10 may further include a different number of LEDs 10 (e.g., one or more), and may have LEDs 10 of varying output power. Additionally, the chamber 230 volume of each of the reactors 10 may vary.

Illustrative embodiments may position the in-series arrangement 330 and/or the in-parallel arrangement 340 in-line, within, and/or between the ends a straw (e.g., a metallic drinking straw). The parallel and/or in-series arrangements of reactors 10 (e.g., minireactors) can be used to great advantage. Rather than redesigning a new reactor to treat different flow rates or to obtain higher log reduction, the engineer can simply combine identical reactors 10 as needed to obtain the desired flow and log reduction needed for a particular application. This allows greater flexibility in design and arrangement of the total disinfection reactor system and lower costs in manufacturing with higher volumes. Additionally, the small reactors 10 using a single small UVC light source (such as a single UVC LED as described above) are easier to design because the fluid flow is confined to a small reactor volume, which ensures more uniform treatment.

Larger reactor volumes (e.g., to achieve higher flow rates) with multiple UVC radiation sources (e.g. to increase the log reduction of the reactor) are carefully designed to ensure that all of the fluid which passes through the reactor receives the same UVC fluence (or dose). This is especially problematic in situations where it is desired to obtain a high log reduction since a small amount of fluid which receives a lower fluence will contaminate the overall fluid which may have received a higher fluence. As described previously, in contrast, the small chamber volume substantially reduces the likelihood of fluid passing through without receiving a substantially uniform fluence.

By combining the small reactors 10, a range of fluid flows from, for example, 0.5 L/min to 30 L/min and a fluence of, for example, 10 $mJ/cm^2$ to 200 $mJ/cm^2$ can be achieved (corresponding to about a 1 log reduction to about an 8 log reduction depending on the pathogen). Even values outside of these ranges can be achieved. However, particularly at higher flows, illustrative embodiments may be more cost effective to build a single reactor with multiple UVC light sources (when the sum total cost of the individual small reactors greatly exceed the cost of making the single larger reactor).

Each of the reactors 10 may be controlled by a single controller. All of the reactors 10 may have identical LED duty cycles and may be activated simultaneously. Alternatively, each reactor 10 may be activated by fluid flow. In such embodiments, the reactor 10 closer to the fluid input is activated prior to a downstream reactor. Additionally, or alternatively, all of the reactors 10 may be periodically dosed by operating the UVC LEDs periodically.

Furthermore, to enable ease of connections and variations in the various configurations of reactors 10, the reactors 10 may have threaded male and female components (e.g., inputs and outputs) configured to provide for easy coupling between reactors 10. In various embodiments, the various reactors may use any standard plumbing or pneumatic connection known in the art.

Figure 11E:
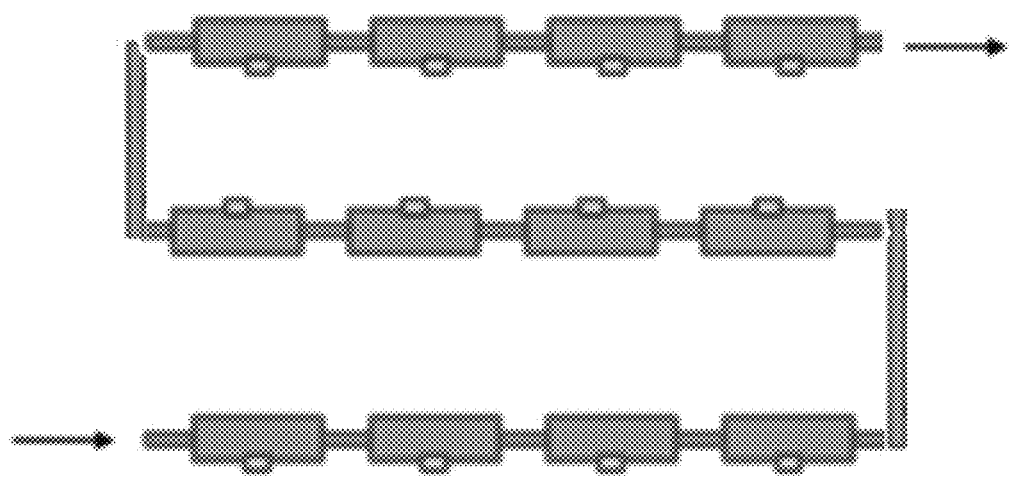

FIG. 11E schematically shows an arrangement 360 of a winding in-series arrangement in accordance with illustrative embodiments of the invention. As shown, various embodiments may position the reactors 10 in different arrangements. FIG. 11E is an example of an arrangement that provides a large log-reduction effect and takes up a relatively small footprint. One of skill in the art can envision other arrangements of reactors 10 that are within the scope of illustrative embodiments.

Figure 12:
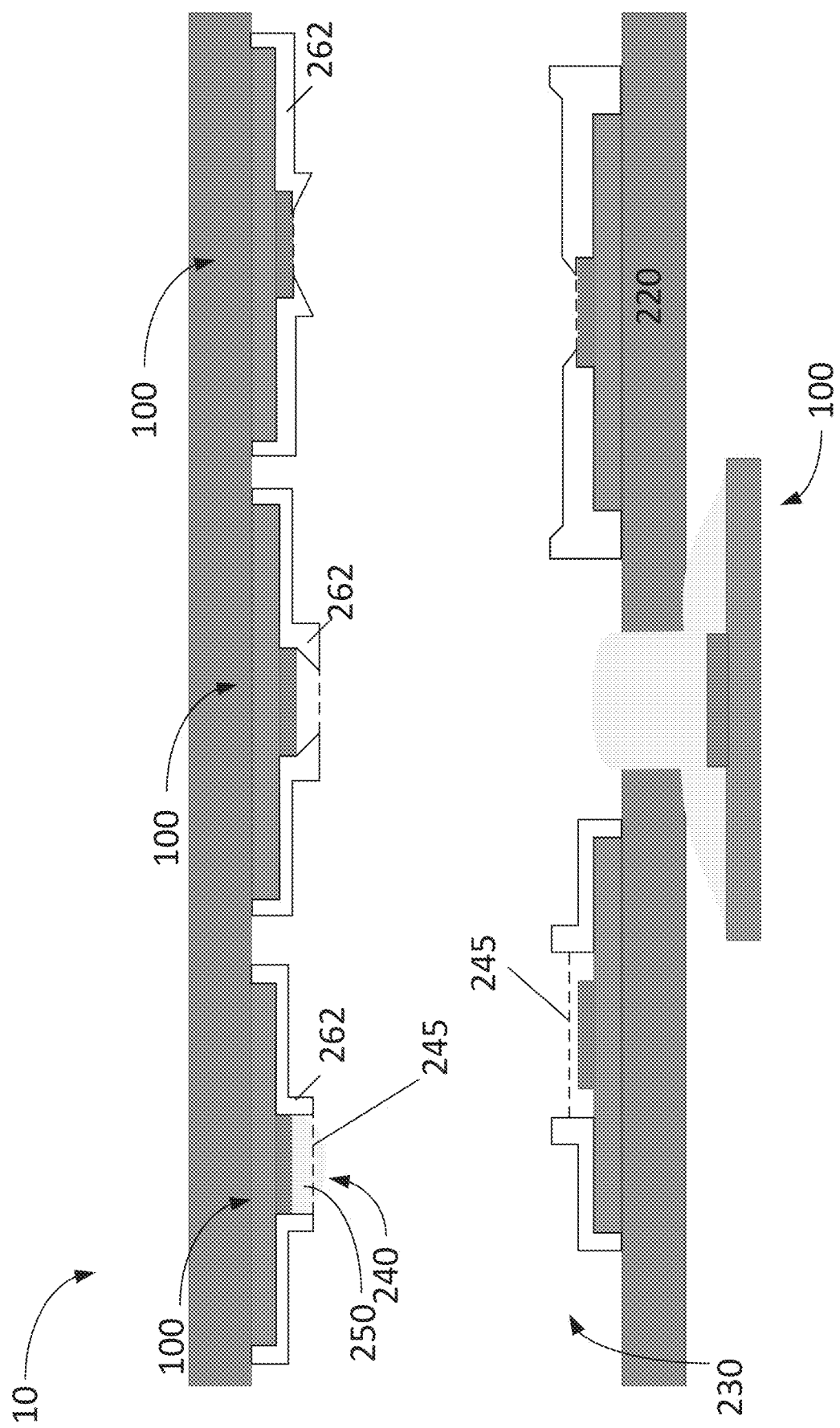
FIG. 12 schematically shows a sectional view of an alternative embodiment of the UV reactor in accordance with illustrative embodiments of the invention.

FIG. 12 schematically shows a sectional view of an alternative embodiment of the UV reactor in accordance with illustrative embodiments of the invention. In the alternative embodiment, the aperture 240 is formed by an LED cover 262 in accordance with illustrative embodiments of the invention. LEDs 100 having the cover 262 may be similar to, and have similar components, and previously described LEDs 100. For example, the LED 100 may have a chip 110, a package 120, and be used with an optical coupler 250. However, in various embodiments, the aperture 240 may be formed by the cover 262. Indeed, as shown, some LEDs 100 may not have an aperture through the wall 220 of the chamber 230.

As described previously, each of the apertures 240 has an aperture area 245. The aperture area 245 may be defined by a length and a width, a diameter, and/or a radius and angle, among other things. While illustrative embodiments provide various examples for defining the aperture area 245, it should be understood that the aperture 240 may take any shape, and is not limited to a rectangular, circular, or semi-circular cross-section.

As described previously, the aperture 240 area 245 may be the smallest area of the aperture 240. The area 245 of the aperture 240 acts as an absorber (by letting light escape and/or become absorbed by the die 110, the package 120, and/or other components) compared to the total reflective area of the chamber 230. For example, in some embodiments, the aperture area 245 may be defined by the area at the end of the aperture 240 (e.g., in the case where the aperture extends out of the chamber 230 as in FIG. 4). Accordingly, the cover 262 provides the smallest area 245 through which the UVC radiation is emitted. In some embodiments, the cover 262 may be formed from the same material as the wall 220 and/or be an integral part of the wall 220.

In various embodiments, the aperture 240 may be formed from UVC reflective and/or UVC absorbent material. Furthermore, in some embodiments, the aperture 240 may be the same size or smaller than the LED chip 110 (i.e., the aperture area 245 is the same size or smaller than the top radiation emission surface 150 area). Preferably, the cover 262 is made of a UVC reflective material, reducing the amount of radiation that is otherwise absorbed by the LED die 110, the package 120, and/or the wall 220.

Figure 13A:
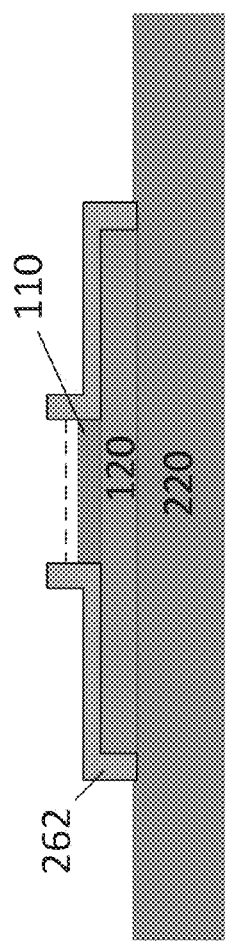
FIGS. 13A-13E schematically show various alternative embodiments of covers for the LED in accordance with illustrative embodiments of the invention
Figure 13B:
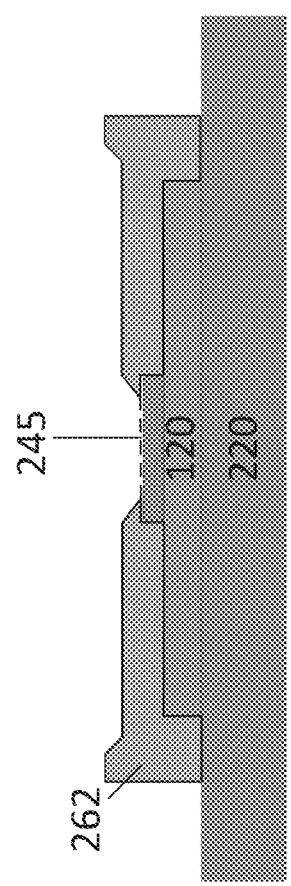
Figure 13C:
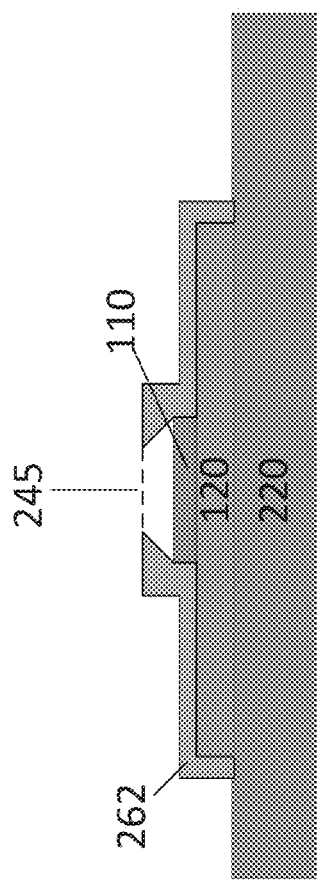
Figure 13D:
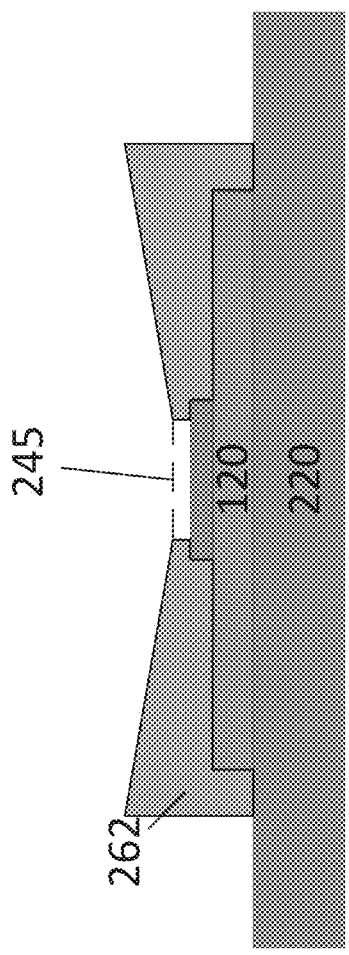
Figure 13E:
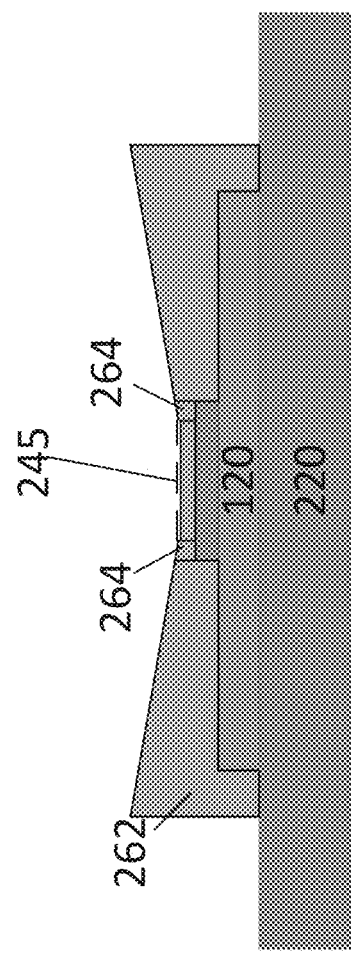

FIGS. 13A-13E schematically show various alternative embodiments of covers 262 for the LED 100 in accordance with illustrative embodiments of the invention. In FIG. 13B, the aperture area 245 is the exposed portion of the radiation emission surface 150 of the chip 110. In FIG. 13C, the aperture area 245 is the smallest opening of the cover 262. In FIG. 13D, the aperture area 245 is the smallest opening of the cover 262. FIG. 13E shows an embodiment similar to FIG. 13D, except the cover 262 includes a UVC transparent portion 264. However, the UVC transparent portion 264 does not obstruct the emission of UVC into the chamber 230, and therefore, is not considered to limit the size of the aperture area 245 (in a similar way that the optical coupler 250 does not limit the size of the aperture area 245). Accordingly, the embodiments shown in FIGS. 13D and 13E are considered to have the same aperture area 245.

Although the above discussion discloses various exemplary embodiments of the invention, it should be apparent that those skilled in the art can make various modifications that will achieve some of the advantages of the invention without departing from the true scope of the invention.

What is claimed is:

1. A system for disinfecting fluid, the system comprising: a plurality of fluid reactors, each of the fluid reactors having:
   a UVC LED including an LED chip configured to emit UVC radiation and a package coupled with the LED chip, the LED chip having a top surface defining a chip top surface area, the top surface being formed from a semiconductor material having an index of refraction;
   at least one wall defining a chamber configured to contain the fluid;
   an aperture configured to receive UVC radiation into the chamber, the aperture having an aperture area, the aperture area being smaller than a top surface area of the package.

2. The system as defined by claim 1, wherein the plurality of reactors are arranged in-series.

3. The system as defined by claim 1, wherein the plurality of reactors are arranged in parallel.

4. The system as defined by claim 1, wherein the plurality of reactors includes a plurality of in-series reactors in parallel.

5. The system as defined by claim 1, wherein the UVC LED is of the type having an exposed top surface.

6. The system as defined by claim 1, wherein the aperture is formed by the at least one wall.

7. The system as defined by claim 1, wherein the aperture is formed by a cover.

8. The system as defined by claim 7, wherein the cover is UVC reflective.

9. The system as defined by claim 7, wherein the cover includes a UVC transparent portion.

10. The system as defined by claim 1, further comprising an optical coupler configured to contact at least a portion of the LED and to form a fluid seal with the aperture, the optical coupler being UV transparent, and having an index of refraction that is greater than an index of refraction of water.

11. The system as defined by claim 10, wherein the optical coupler intimately contacts the LED chip.

12. The system as defined by claim 1, wherein the aperture area is equal to or larger than the chip top surface area.

13. A system for disinfecting fluid using UVC LEDs, the system comprising:
- a plurality of UVC LEDs, each of the UVC LEDs including an LED chip configured to emit UVC radiation and a package coupled with the LED chip, each of the LED chips having a respective radiation emission surface;
- a plurality of fluid reactors, each of the fluid reactors having at least one wall defining a chamber configured to house the fluid therein, the at least one wall defining a wall area, the chamber having a fluid volume of between about 0.004 cm$^3$ and about 20.0 cm$^3$, each of the reactors having an aperture through which the emitted UVC radiation enters the chamber, the aperture having an aperture area, the wall area and the aperture area adding to produce a total area, the aperture area being between 0.0001% and 17% of total area.

14. The system as defined by claim 13, further comprising:
- an optical coupler configured to optically couple the UVC LED and the fluid reactor, the optical coupler being (1) UV transparent, and (2) having an index of refraction that is greater than the index of refraction of the fluid, the optical coupler being positioned between the chamber and the LED chip.

15. The system as defined by 13, wherein the plurality of reactors are arranged in-series and/or in-parallel.

16. The system as defined by claim 15, wherein the aperture is formed by a cover.

17. The system as defined by claim 13, wherein the aperture area is greater than about 0.025% of the total area.

18. The system as defined by claim 13, wherein the aperture area is less than about 0.77% of the total area.

19. A method of fluid treatment, the method comprising:
providing:
- a plurality of fluid reactors positioned in-series and/or in-parallel, each of the reactors having at least one wall defining a chamber configured to house fluid therein, the at least one wall defining a wall area, the chamber having a fluid volume of between about 1 cm$^3$ and about 10 cm$^3$, each of the reactors having an aperture through which the emitted UVC radiation enters the chamber, the aperture having an aperture area, the wall area and aperture area adding to produce a total area, the aperture area being between about 0.0001 percent and about 17 percent of the total area;
- a respective UVC LED configured to emit UVC radiation into a respective fluid reactor, the UVC LED including an LED chip configured to emit UVC radiation and a package coupled with the LED chip, the LED chip having a radiation emission surface;

positioning an optical coupler in the aperture between the UVC LED and the chamber in each reactor, disinfecting the fluid in each reactor by activating the respective UVC LED.

20. The method as defined by claim 19, wherein all of the LEDs are dosed simultaneously.

* * * * *